US008481664B2

(12) United States Patent
Dairoku et al.

(10) Patent No.: US 8,481,664 B2
(45) Date of Patent: Jul. 9, 2013

(54) PARTICULATE WATER ABSORBING AGENT INCLUDING POLYACRYLIC ACID (POLYACRYLATE) BASED WATER ABSORBING RESIN AS A PRINCIPAL COMPONENT, METHOD FOR PRODUCTION THEREOF, WATER-ABSORBENT CORE AND ABSORBING ARTICLE IN WHICH THE PARTICULATE WATER ABSORBING AGENT IS USED

(75) Inventors: Yorimichi Dairoku, Himeji (JP); Hirotama Fujimaru, Himeji (JP); Kunihiko Ishizaki, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 1001 days.

(21) Appl. No.: 11/911,169

(22) PCT Filed: Apr. 11, 2006

(86) PCT No.: PCT/JP2006/308002
§ 371 (c)(1),
(2), (4) Date: Aug. 21, 2009

(87) PCT Pub. No.: WO2006/109882
PCT Pub. Date: Oct. 19, 2006

(65) Prior Publication Data
US 2009/0318885 A1 Dec. 24, 2009

(30) Foreign Application Priority Data
Apr. 12, 2005 (JP) .................. 2005-114788

(51) Int. Cl.
*C08F 20/06* (2006.01)
*A61F 13/15* (2006.01)
*A61F 13/20* (2006.01)

(52) U.S. Cl.
USPC .......... 526/317.1; 604/358; 604/369

(58) Field of Classification Search
USPC ............ 525/329.7; 524/332; 526/317.1, 526/348; 604/358, 369; 521/64
See application file for complete search history.

(56) References Cited

U.S. PATENT DOCUMENTS

| | | |
|---|---|---|
| 4,093,776 A | 6/1978 | Aoki et al. |
| 4,286,082 A | 8/1981 | Tsubakimoto et al. |
| 4,367,323 A | 1/1983 | Kitamura et al. |
| 4,446,261 A | 5/1984 | Yamasaki et al. |
| 4,625,001 A | 11/1986 | Tsubakimoto et al. |
| 4,654,039 A | 3/1987 | Brandt et al. |
| 4,683,274 A | 7/1987 | Nakamura et al. |
| 4,873,299 A | 10/1989 | Nowakowsky et al. |
| 4,973,632 A | 11/1990 | Nagasuna et al. |
| 4,985,518 A | 1/1991 | Alexander et al. |
| 5,124,416 A | 6/1992 | Haruna et al. |
| 5,145,906 A | 9/1992 | Chambers et al. |
| 5,244,735 A | 9/1993 | Kimura et al. |
| 5,250,640 A | 10/1993 | Irie et al. |
| 5,264,495 A | 11/1993 | Irie et al. |
| 5,380,808 A | 1/1995 | Sumiya et al. |
| 5,385,983 A | 1/1995 | Graham |
| 5,409,771 A | 4/1995 | Dahmen et al. |
| 5,439,993 A | 8/1995 | Ito et al. |
| 5,462,972 A | 10/1995 | Smith et al. |
| 5,478,879 A | 12/1995 | Kajikawa et al. |
| 5,562,646 A | 10/1996 | Goldman et al. |
| 5,571,386 A | 11/1996 | Bauer, Jr. et al. |
| 5,597,873 A | 1/1997 | Chambers et al. |
| 5,610,220 A | 3/1997 | Klimmek et al. |
| 5,633,316 A | 5/1997 | Gartner et al. |
| 5,674,633 A | 10/1997 | Saunders et al. |
| 5,744,564 A | 4/1998 | Stanley, Jr. et al. |
| 5,985,944 A * | 11/1999 | Ishizaki et al. .......... 521/64 |
| 6,071,976 A | 6/2000 | Dairoku et al. |
| 6,228,930 B1 | 5/2001 | Dairoku et al. |
| 6,254,990 B1 | 7/2001 | Ishizaki et al. |
| 6,359,049 B1 | 3/2002 | Carrico et al. |
| 6,444,744 B1 | 9/2002 | Fujimaru et al. |
| 6,469,080 B2 | 10/2002 | Miyake et al. |
| 6,472,478 B1 | 10/2002 | Funk et al. |
| 6,503,979 B1 | 1/2003 | Funk et al. |
| 6,617,489 B2 | 9/2003 | Wada et al. |
| 6,620,889 B1 | 9/2003 | Mertens et al. |
| 6,964,998 B2 | 11/2005 | Wada et al. |
| 7,179,875 B2 | 2/2007 | Fuchs et al. |
| 2003/0207997 A1 | 11/2003 | Mertens et al. |
| 2004/0110897 A1 | 6/2004 | Sakamoto et al. |
| 2004/0110913 A1 | 6/2004 | Kanto et al. |
| 2004/0110914 A1 | 6/2004 | Nakahara et al. |
| 2005/0209352 A1 | 9/2005 | Dairoku et al. |
| 2005/0209411 A1 | 9/2005 | Nestler et al. |
| 2006/0036043 A1 | 2/2006 | Nestler et al. |
| 2006/0089512 A1 | 4/2006 | Bennett et al. |
| 2008/0119626 A1 * | 5/2008 | Fujimaru et al. .......... 526/317.1 |

FOREIGN PATENT DOCUMENTS

| | | |
|---|---|---|
| CA | 2319786 | 8/1999 |
| DE | 199 09 653 | 9/2000 |
| EP | 0349240 | 1/1990 |
| EP | 0450923 | 10/1991 |
| EP | 0450924 | 10/1991 |
| EP | 0574260 | 12/1993 |

(Continued)

*Primary Examiner* — Ling Choi
*Assistant Examiner* — Monique Peets
(74) *Attorney, Agent, or Firm* — Roylance, Abrams, Berdo & Goodman, L.L.P.

(57) ABSTRACT

As a characteristic that had not been known conventionally at all, "permeability potential under pressure (PPUP)" of a particulate water absorbing agent is regulated, and further, "range of particle size distribution" and "coloring" are concomitantly regulated. The present invention is directed to a particulate water absorbing agent having the following (a) to (c):

(a) permeability potential under pressure (PPUP) being 50 to 100%;
(b) yellowness index (YI) being 0 to 10, and rate of change of yellowness index (ΔYI) being 100 to 150% following a coloring acceleration test for 14 days at 70±1° C. and the relative humidity of 95±1%; and
(c) particles of smaller than 150 μm specified by standard sieve classification accounting for 0 to 5% by weight, weight average particle diameter (D50) being 200 to 550 μm, and logarithmic standard deviation (σζ) of particle size distribution being 0.20 to 0.40.

10 Claims, No Drawings

FOREIGN PATENT DOCUMENTS

| | | |
|---|---|---|
| EP | 0605150 | 7/1994 |
| EP | 0668080 | 8/1995 |
| EP | 0811636 | 12/1997 |
| EP | 0812873 | 12/1997 |
| EP | 0922717 | 6/1999 |
| EP | 0937736 | 8/1999 |
| EP | 0942014 | 9/1999 |
| EP | 0955086 | 11/1999 |
| EP | 1108745 | 6/2001 |
| EP | 1178059 | 2/2002 |
| EP | 1199059 | 4/2002 |
| EP | 1302485 | 4/2003 |
| EP | 1457541 | 9/2004 |
| JP | 62273283 | 11/1987 |
| JP | 03031306 | 2/1991 |
| JP | 04331205 | 11/1992 |
| JP | 05086251 | 4/1993 |
| JP | 06211934 | 8/1994 |
| JP | 07242709 | 9/1995 |
| JP | 2000327926 | 11/2000 |
| JP | 2003052742 | 2/2003 |
| JP | 2004315816 | 11/2004 |
| JP | 2004323606 | 11/2004 |
| WO | 9942494 | 8/1999 |
| WO | 9942496 | 8/1999 |
| WO | 9943720 | 9/1999 |
| WO | 03014172 | 2/2003 |
| WO | 03051940 | 6/2003 |
| WO | 03095510 | 11/2003 |
| WO | 2004052819 | 6/2004 |
| WO | 2004052949 | 6/2004 |
| WO | 2004069404 | 8/2004 |
| WO | 2004084962 | 10/2004 |
| WO | 2004085496 | 10/2004 |

* cited by examiner

PARTICULATE WATER ABSORBING AGENT INCLUDING POLYACRYLIC ACID (POLYACRYLATE) BASED WATER ABSORBING RESIN AS A PRINCIPAL COMPONENT, METHOD FOR PRODUCTION THEREOF, WATER-ABSORBENT CORE AND ABSORBING ARTICLE IN WHICH THE PARTICULATE WATER ABSORBING AGENT IS USED

TECHNICAL FIELD

The present invention relates to a particulate water absorbing agent including a water absorbing resin as a principal component, a method for production of the same, a water-absorbent core and an absorbing article in which this particulate water absorbing agent is used. More particularly, the present invention relates to a particulate water absorbing agent for absorbent cores which may be used in disposable diapers, sanitary napkins and the like, the particulate water absorbing agent being excellent in the yellowing preventive performance, and having excellent absorption ability not found in conventional products.

BACKGROUND ART

In recent years, water absorbing resins having excellent water absorbing properties have been developed, and have been heavily used in predominantly applications for disposable items as in absorbing articles such as disposable diapers and sanitary napkins, as well as water retention agents for use in agriculture and horticulture water retention agent, industrial water cut-off materials, and the like. In such water absorbing resins, variety of monomers and hydrophilic polymers have been proposed as raw materials. Among them, polyacrylic acid (polyacrylate) based water absorbing resins in which acrylic acid and/or a salt thereof is used as a monomer have been industrially used most often in light of their superior absorption performances.

Conventionally, known water-absorption properties expected for the water absorbing resin as described above involve many characteristics (parameters) such as centrifuge retention capacity, absorbency against pressure, water-absorption speed, liquid permeability without pressure, liquid permeability under pressure, impact resistance, resistance to urine, flowability, gel strength, color, range of particle size distribution and the like. In addition, with regard to the same physical property (e.g., centrifuge retention capacity), many definitions according to various aspects (parameter measurement methods) were proposed.

As water absorbing resins (particulate water absorbing agents) which have been developed while focusing on these many physical properties, those targeted to or specified for these physical properties have been also produced and used. However, even though the aforementioned numerous physical properties (e.g., "centrifuge retention capacity", "absorbency against pressure" and the like) were controlled, there still exists a problem of hardly achieving sufficient performance in practical applications in absorbent cores such as disposable diapers and the like.

Hereinafter, conventionally targeted physical properties of water absorbing resins and means for achieving them will be explained.

Because water absorbing resins are used generally in applications for disposable items (disposable diapers and the like), they must be necessarily inexpensive. Hence, improvement of productivity has been strongly desired. Also, according to use in absorbing articles, they are expected to be free from problems involving safety and coloring, as a matter of course. More specifically, because unreacted acrylic acid remains in water absorbing resins although in an amount of several hundreds to thousands ppm by weight, lowering of its amount has been desired. Furthermore, since water absorbing resins are combined with white pulp in absorbing articles, they per se are expected to be white colored so as to avoid unusual feeling due to coloring.

Additionally, water absorbing resins have water-swelling property as well as water insolubility. However, as described in Document 1, uncrosslinked water soluble polymer (extractables in water) is included in the water absorbing resin in an amount of several % by weight to several ten % by weight, and these extractables adversely affect water-absorption properties. Therefore, lowering of the amount of the extractables in water has been desired. Moreover, as described in Document 2, physical properties under pressure such as absorbency against pressure and liquid permeable amount under pressure have been desired for water absorbing resins or particulate water absorbing agent (or particulate form water absorbing materials) in absorbing articles.

In attempts to solve the problems as described above, a process in which polymerization is carried out after purification of monomer to give the heavy metal content of not higher than 0.1 ppm (Document 3), a process in which acrylic acid including less acrylic acid dimer oligomer is used (Documents 4, 5), a process in which polymerization is carried out after purification of acrylic acid to give the content of acetic acid and propionic acid of lower than 400 ppm (Document 6), a process in which acrylic acid including less protoanemonen is used (Document 7), a process in which acrylic acid including less furfural is used (Document 8), a process in which acrylic acid including less hydroquinone is used (Document 9) and the like were proposed. Additionally, as the process for lowering impurities in raw materials of a water absorbing resin, a process in which acrylic acid is treated with an aldehyde treating agent (Document 10), a process in which acrylic acid is treated with activated charcoal (Document 11) were proposed.

Although processes for attaining a water absorbing resin having superior physical properties by a method for production in which a raw material, acrylic acid or the like, is highly purified have been proposed as in Documents 3 to 11, there existed problems involving cost and productivity.

Furthermore, for improving physical properties, a process for polymerization of a water absorbing resin in this a certain amount of a minor component is added was proposed. For example, a process in which methoxyphenols included in acrylic acid are adjusted to 10 to 160 ppm (Document 12), a process in which furfural in an amount of 11 to 2000 ppm is allowed to coexist (Document 13), a process in which a metal is used (Documents 14, 15) and the like were proposed. However, according to the process described in Documents 12 and 13, methoxyphenol or furfural included in the monomer which may cause oxidative coupling during the production step of the water absorbing resin could result in a problem of coloring (yellowing) of the water absorbing resin thus obtained.

Moreover, in order to solve the problems described above, a process in which polymerization is carried out with a reversed phase suspension polymerization method using hydroxyperoxide and a reducing agent, followed by a treatment with a silane coupling agent (Document 16), a process in which an organic phosphorus compound is incorporated (Document 17), a process for production in which an inorganic reducing agent such as hypophosphorous acid is incorporated (Document 18), a process in which a treatment with an organic carboxylic acid (salt) is conducted (Document 17), a process in which a treatment with a reductive compound and an inorganic or organic acid is conducted (Document 20), a process in which a sulfinic acid derivative is used as a polymerization initiator (Document 21) were proposed. However, any process involved problems of cost and productivity slowdown. Additionally, when the water absorbing resin was used at a high concentration, there existed problems in absorption properties such as liquid permeability and incorporation of the liquid to be absorbed such as urine Furthermore, a technique for improving liquid permeability of water absorbing resins in absorbent cores and breathability of the absorbent cores through regulating the average particle diameter to fall within the range of 400 to 850 μm (Document 22) was proposed. However, when the water absorbing resin was used in the absorbent core at a high concentration using this technique, the liquid permeability was elevated, while unsanitary impression may be made to consumers due to coarse particles, and to conspicuous yellowing of the water absorbing resin per se.

Moreover, in addition to the aforementioned procedures, a process for producing a water absorbing resin using an ammonium salt as a counter ion of carboxylic acid in order to improve various physical properties of the water absorbing resin (Document 23 to 25) was proposed. However, there existed problems of coloring (yellowing) of the resulting water absorbing resin, and it was still insufficient in terms of solution of the aforementioned various problems.

Also, heretofore, when the water absorbing resin particles have a small average particle diameter, for example, when the particle diameter is less than 150 μm, in particular, when particles of smaller than 45 μm account for not less than 5% by weight, particularly beyond 10% by weight, such a particulate water absorbing agent inhibits liquid permeability because gel blocking is caused, although a white-colored state resulting from scattering of visible light may be exhibited. Hence, "characteristic of maintaining a white-colored state" and "liquid permeability characteristic" of the particles are contradictory parameters.

(Document 1) U.S. Pat. No. 4,654,039
(Document 2) U.S. Pat. No. 55,662,646
(Document 3) JP-A No. H3-31306
(Document 4) JP-A No. H6-211934
(Document 5) International Publication No. WO04/52949
(Document 6) International Publication No. WO03/95510
(Document 7) European Patent No. 1302485
(Document 8) United States Patent Publication No.
(Document 9) U.S. Pat. No. 6,444,744
(Document 10) International Publication No. WO03/14172
(Document 11) International Publication No. WO04/52819
(Document 12) United States Patent Publication No. 2004/0110914
(Document 13) United States Patent Publication No. 2004/0110897
(Document 14) U.S. Pat. No. 5,439,993
(Document 15) European Patent No. 1457541
(Document 16) JP-A No. H4-331205
(Document 17) JP-A No. H5-86251
(Document 18) U.S. Pat. No. 6,359,049
(Document 19) JP-A No. 2000-327926
(Document 20) JP-A No. 2003-52742
(Document 21) International Publication No.
(Document 22) U.S. Pat. No. 6,617,489
(Document 23) JP-A No. S62-273283
(Document 24) JP-A No. 2004-315816
(Document 25) JP-A No. 2004-323606

DISCLOSURE OF THE INVENTION

In particulate water absorbing agents including a water absorbing resin as a principal component, an object in connection with the problem to be solved by the present invention is to provide a particulate water absorbing agent for use in an absorbent core, which can achieve sufficient absorption performance for use in absorbent cores at a high concentration, and further, is suitable for practical applications.

Under the circumstances in which numerous water absorbing resins (particulate water absorbing agents) having regulated parameter physical properties have been proposed, the present inventors newly focused on characteristics of "permeability potential under pressure (PPUP)" of the water absorbing resin from completely novel perspectives. Moreover, the present inventors found that this novel characteristic (PPUP) is an important factor in practical applications of water absorbing resins.

Then, the present inventors found that a particulate water absorbing agent in which "coloring" and "range of particle size distribution" in addition to the "permeability potential under pressure (PPUP)" which is a characteristic that had not been conventionally known at all are regulated to fall within a certain range will be a water absorbing resin (particulate water absorbing agent) which can be optimally used in absorbent cores in practical applications. Accordingly, the present invention was accomplished.

Hence, the particulate water absorbing agent of the present invention is a particulate water absorbing agent comprising a water absorbing resin having a constitutional unit derived from acrylic acid and a salt thereof, and has:

(a) permeability potential under pressure (PPUP) being 50 to 100%;

(b) yellowness index (YI) being 0 to 10, and rate of change of yellowness index (ΔYI) being 100 to 150% as measured with a coloring acceleration test for 14 days in an atmosphere of the temperature being 70±1° C. and the relative humidity being 95±1%; and (c) particles of smaller than 150 μm specified by standard sieve classification accounting for 0 to 5% by weight, weight average particle diameter (D50) specified by standard sieve classification being 200 to 550 μm, and logarithmic standard deviation (σζ) of particle size distribution specified by standard sieve classification being 0.20 to 0.40, wherein permeability potential under pressure (PPUP) is specified by the following formula:

$$PPUP(\%) = (AAP:5.0\ g)/(AAP:0.90\ g)*100$$

wherein (AAP: 0.90 g) is the absorbency against pressure measured with 0.90 g of the particulate water absorbing agent for a 0.90% by weight aqueous sodium chloride solution under a pressure of 4.8 kPa for 60 min; and (AAP: 5.0 g) is the absorbency against pressure measured with 5.0 g of the particulate water absorbing agent for a 0.90% by weight aqueous sodium chloride solution under a pressure of 4.8 kPa for 60 min.

The particulate water absorbing agent of the present invention achieves excellent absorption ability (excellent liquid permeability, low amount of residual monomer, excellent coloring preventive characteristic) which had not been found conventionally, in practical applications in absorbing article such as diapers, and particularly, in use of the water absorbing resin at a high concentration. In the present specification, the terms "weight average particle diameter" are synonymous with the terms "mass average particle diameter". In the present specification, the terms "part by weight" and "% by weight" are synonymous with the terms "part by mass" and "% by mass", respectively.

BEST MODE FOR CARRYING OUT THE INVENTION

Hereinafter, the present invention will be explained in more detail.

(1) Water Absorbing Resin

The water absorbing resin which may be used in the particulate water absorbing agent of the present invention has a constitutional unit derived from acrylic acid. Preferably, this water absorbing resin has a constitutional unit derived from acrylic acid as a principal component. More preferably, the constitutional unit derived from acrylic acid accounts for not less 90 mol % of than total constitutional unit number of this water absorbing resin. Process for producing this water absorbing resin is not particularly limited, but preferably, this water absorbing resin may be obtained by polymerization of a monomer component including acrylic acid and/or a salt thereof as a principal component. The aforementioned constitutional unit derived from a monomer corresponds to, for example, a structure of each monomer with the polymerizable double bond being opened upon polymerization. The structure with the polymerizable double bond being opened refers to, for example, a structure yielded by turning carbon-carbon double bond (C=C) into a single bond (—C—C—).

Crosslinked water absorbing resin which may be used in a particulate water absorbing agent referred to herein means a water-swelling and water insoluble polymer prepared by introducing a cross-linked structure to a polymer. The water-swelling property refers to have a centrifuge retention capacity (absorption capacity under no compression, GVs) for a physiological saline solution being not less than 2 times, preferably 5 to 200 times, and more preferably 20 to 100 times. Furthermore, the water insolubility refers to substantial water insolubility which exhibits water extractables in the resin being essentially 0 to not more than 50% by weight, preferably 0 to 25% by weight, more preferably 0 to 15% by weight, and still more preferably 0 to 10% by weight. Measurement method of these properties will be specified in Examples described later.

Moreover, in the present invention, the polyacrylic acid (polyacrylate) based water absorbing resin refers to one having a total mol % of acrylic acid and/or salts thereof in the entire monomer used in polymerization (except for crosslinking agent) being essentially 50 to 100 mol %, more preferably 70 to 100 mol %, still more preferably 100 to 90 mol %, and particularly preferably 100 mol % in effect.

Examples of the acrylate salt which may be generally used in the present invention include monovalent salts of acrylic acid, e.g., salts of alkali metal such as lithium, sodium and potassium; ammonium salts; amine salts, and the like. Preferably, an acrylate salt including acrylate ammonium salt or an amine salt as a principal component may be used. Moreover, an acrylate alkali metal salt and an acrylate ammonium salt or amine salt may be used in combination. In such an instance, ratio (mol %) of the acrylate ammonium salt or amine salt in total amount of used acrylate salt (moles) may be preferably 50 to 100 mol %, preferably 60 to 100 mol %, more preferably 70 to 100 mol %, and most preferably 90 to 100 mol %. The acrylate ammonium salt or amine salt accounting for less than 50 mol % of total amount of the acrylate salt is not preferred because the yellowing (coloring) preventive effect may be suppressed. Additionally, a polyvalent metal salt such as a calcium salt or an aluminum salt may be used in combination in the range to allow a water-swelling property to be achieved. When acrylic acid is neutralized before the polymerization, the ratio (mol %) of the aforementioned acrylate ammonium salt or amine salt shall be the ratio (mol %) per the entire monomer component before the polymerization. When acrylic acid is neutralized during or after the polymerization of the monomer component, the ratio (mol %) of the aforementioned acrylate ammonium salt or amine salt shall be the ratio (mol %) per number of the constitutional units of the monomer component in the polymer. The number of the constitutional units of the monomer component is equivalent to the number of molecules of the polymerized monomer.

The water absorbing resin obtained in the present invention has a neutralization ratio of preferably 10 to 99 mol % per the acid group, more preferably acid group 20 to 99 mol %, more preferably 40 to 95 mol % per the acid group, still more preferably 40 to 90 mol % per the acid group, particularly preferably 50 to 90 mol % per the acid group, and most preferably 60 to 80 mol % per the acid group.

This neutralization may be carried out on the monomer component prior to the polymerization, or may be carried out during or after the polymerization. Otherwise, neutralization of the monomer component and neutralization of the polymer may be carried out in combination. Preferably, an alkali treatment may be carried out on acrylic acid as a monomer component.

(2) Particulate Water Absorbing Agent and Method for Production of the Same

In the present invention, the particulate water absorbing agent refers to an absorption and fixation agent for an aqueous liquid which includes a water absorbing resin (as a principal component), and preferably contains water, more preferably a certain amount of water (moisture content being 0.1 to 10% by weight, and still preferably 2 to 8% by weight) The content of the water absorbing resin is preferably 70 to 98% by weight, more preferably 80 to 98% by weight, and more preferably 90 to 98% by weight per the total of particulate water absorbing agent. Also, the additive described later may be used as needed. The aqueous liquid is not limited to water, but examples thereof include blood, feces, waste liquid, moisture and vapor, ice, mixture of water and an organic solvent or an inorganic solvent, rainwater and groundwater, without particular limitation thereto as long as they include water. The particulate water absorbing agent of the present invention may be preferably, an absorption and fixation agent for urine, particularly for human urine.

In the present invention, the particle shape is not particularly limited. Illustrative examples of the particle shape include spherical shape, suborbicular shape, elliptical shape, irregularly pulverized shape, rod-like shape, polyhedron-like shape, sausage-like shape (illustrated in U.S. Pat. No. 4,973,632) and creased shape (illustrated in U.S. Pat. No. 5,744,564). The particle may be a single particle, a agglomerate particle or mixture thereof. The particle may be a foamed porous. The single particle or the agglomerate particle of irregularly pulverized shape are illustrated preferably as the particle.

In an exemplary method for the production of a particulate water absorbing agent of the present invention, the particulate water absorbing agent may be obtained by, for example, a method for production comprising the following steps (A) to (C). It is preferred that acrylic acid used in the method for the production of the particulate water absorbing agent of the present invention includes a slight amount of the minor component described later.

Step (A): a step of preparing a monomer component including acrylic acid and/or a salt thereof as a principal component, wherein at least a part of the acrylate salt is an ammonia salt and/or amine salt.

Step (B): a step of carrying out aqueous polymerization of the monomer component with an azo polymerization initiator.

Step (C): a step of obtaining dry powder following the polymerization, the powder including particles of smaller than 150 μm at a percentage of 0 to 5% by weight, with a weight average particle diameter (D50) of 200 to 450 μm, and with logarithmic standard deviation (σζ) of the particle size distribution being 0.20 to 0.40.

Step (D): a step of carrying out surface crosslinking of the dry powder obtained in the step (C).

The aforementioned method for production is merely an example. The particulate water absorbing agent of the present invention is not limited to the water absorbing agent obtained in the aforementioned method for production as long as the aforementioned characteristics are achieved.

(3) Permeability Potential under Pressure (PPUP)

One aspect of the present invention is that "permeability potential under pressure (PPUP)" that had not been known conventionally at all was specified. In an exemplary production method for allowing this "permeability potential under pressure (PPUP)" to fall within the range as specified above, a water absorbing resin having a certain range of particle size distribution and a certain centrifuge retention capacity is subjected to surface crosslinking with a particular surface crosslinking agent described later.

This permeability potential under pressure (PPUP) is specified by the following formula:

$$PPUP(\%)=(AAP:5.0 \text{ g})/(AAP:0.90 \text{ g})*100$$

wherein, (AAP: 0.90 g) is an absorbency against pressure under a pressure of 4.8 kPa for a 0.90% by weight aqueous sodium chloride solution for 60 min, as measured with 0.90 g of the particulate water absorbing agent; and (AAP: 5.0 g) is an absorbency against pressure under a pressure of 4.8 kPa for a 0.90% by weight aqueous sodium chloride solution for 60 min, as measured with 5.0 g of the particulate water absorbing agent.

Importance of the absorbency against pressure (AAP: 0.9 g) has been known so far, and many types of absorbencies against pressure (AAP: 0.90 g) have been specified through altering measurement time (for example, 5 min to 3 hrs), liquid to be absorbed (for example, various artificial urine, physiological saline solution, ion exchanged water, aqueous L-ascorbic acid solution), load (for example, 0.01 psi to 1.4 psi), measurement particle size distribution in measurement (for example, total particle size distribution/or cut from 600 to 300 μm) and the like. However, unlike such conventional absorbencies against pressure, the permeability potential under pressure (PPUP) according to the present invention concerns the stability of the absorbency against pressure (AAP) when the amount of the water absorbing resin (amount of the resin per unit area of the measurement) is increased from 0.90 g to 5.0 g. In other words, the permeability potential under pressure (PPUP) of the present invention concerns less lowering of the absorbency against pressure (AAP) when the amount of the water absorbing resin (amount of the resin per unit area of the measurement) is increased from 0.90 g to 5.0 g. This permeability potential under pressure (PPUP) is a novel parameter newly specified according to the spirit of the present invention.

Even in cases where absorbency against pressure (AAP) specified by various measurement methods of AAP which had been conventionally proposed was high, conventional water absorbing resins could not achieve sufficient performance in diapers in practical applications. As a result of elaborate investigation of the grounds therefor, the present inventor found that the absorbency against pressure (AAP) varies depending on the amount of the water absorbing resin per unit area even under the same load (compression). Still further, the present inventor found that the amount of the water absorbing resin per unit area partially varies in absorbing articles such as diapers. Moreover, the present inventor found that the variation of the absorbency against pressure (AAP) resulting from the difference (variance) of the amount of the water absorbing resin may be the grounds for deterioration of the physical properties of the absorbing articles such as diapers in practical applications. Accordingly, the present invention was accomplished.

The particulate water absorbing agent of the present invention has very high (PPUP) specified by ((AAP: 5.0 g)/(AAP: 0.90 g)*100), and stably achieves high physical properties in any amount of the water absorbing resin in the diaper (concentration). Further, high liquid permeability may be also achieved.

(4) Acrylic Acid

As the method for the production of acrylic acid which may be used in the present invention, examples of known industrial method for production include a gas phase catalytic oxidation process of propylene and/or acrolein, an ethylene cyanogen hydrin process, a high-pressure Reppe process, a modified Reppe process, a ketene process, an acrylonitrile hydrolysis process and the like. Among these, a gas phase catalytic oxidation process of propylene and/or acrolein has been employed so often. In the present invention, acrylic acid obtained by such a gas phase catalytic oxidation process may be suitably employed. Crude acrylic acid obtained by a gas phase catalytic oxidation process before purification generally contains impurities other than acrylic acid in an amount of not less than about 2000 ppm. The impurities other than acrylic acid will be described later.

In an example of the method for the production of the water absorbing resin according to the present invention, a monomer containing a 10 to 200 ppm of methoxyphenol in terms of the converted value based on acrylic acid is used. Principal component of this monomer may be either acrylic acid, or acrylic acid and an acrylate salt. Illustrative examples of the methoxyphenol include specifically, o, m, p-methoxyphenol, and methoxyphenols derived therefrom to further include one or two or more substituents such as a methyl group, a t-butyl group or a hydroxyl group. Particularly preferably, p-methoxyphenol may be used in the present invention. Content of the methoxyphenol in terms of the converted value based on acrylic acid may be preferably 10 to 100 ppm by weight, preferably 10 to 90 ppm by weight, more preferably 10 to 80 ppm by weight, still more preferably 10 to 70 ppm by weight, particularly preferably 10 to 50 ppm by weight, and most preferably 10 to 30 ppm by weight. When the content of p-methoxyphenol is beyond 200 ppm by weight, a problem of coloring (sallowness/yellowing) of the resulting water absorbing resin may be caused. To the contrary, the content of p-methoxyphenol of lower than 10 ppm by weight, particularly lower than 5 ppm by weight, i.e., in cases where p-methoxyphenol that is a polymerization inhibitor was eliminated by purification such as distillation, is not preferred because there is a risk of occurrence of polymerization before intentionally initiating the polymerization, and surprisingly, polymerization speed is lowered by contrast.

Moreover, in the monomer or particulate water absorbing agent of the present invention, content of protoanemonin and/or furfural is preferably 0 to 20 ppm by weight in terms of the converted value based on acrylic acid. As the content of protoanemonin and/or furfural is increased, polymerization time (time period from addition of the initiator until the polymerization peak temperature is attained) is prolonged to increase the residual monomer, thus resulting in relative deterioration of the physical properties through great increase in water extractables as compared with some increase in water absorption capacity. In light of improvement physical properties and characteristics of the water absorbing resin, content of protoanemonin and/or furfural in the monomer is more preferably not higher than 10 ppm by weight, still more preferably 0.01 to 5 ppm by weight, yet more preferably 0.05 to 2 ppm by weight, and particularly preferably 0.1 to 1 ppm by weight in terms of the converted value based on acrylic acid.

Further, in the monomer or particulate water absorbing agent of the present invention, it is preferred that the amount of aldehyde component other than furfural and/or maleic acid is as small as possible for the same reason. Specifically, the content of the aldehyde component other than furfural and/or maleic acid is preferably 0 to 5 ppm by weight, more preferably 0 to 3 ppm by weight, particularly preferably 0 to 1 ppm by weight, and particularly 0 ppm by weight (not higher than detection limit) in terms of the converted value based on acrylic acid. Examples of the aldehyde component other than furfural include benzaldehyde, acrolein, acetaldehyde and the like.

Additionally, in the monomer or particulate water absorbing agent of the present invention, content of saturated carboxylic acid consisting of acetic acid and/or propionic acid, preferably not higher than 1000 ppm by weight, more preferably 10 to 800 ppm by weight, and particularly preferably 100 to 500 ppm by weight in terms of the converted value based on acrylic acid. Because the saturated carboxylic acid is not polymerized but has volatility, problems of the odor may be caused beyond 1000 ppm. Addition the saturated carboxylic acid in a small amount is preferred since antibiotic properties may be imparted to the water absorbing resin in a safe manner.

Also, as the monomer of the present invention, a polymerization inhibitor other than p-methoxyphenol can be used in the production step. Examples of the efficacious polymerization inhibitor other than p-methoxyphenol include e.g., phenothiazine, hydroquinone, copper salts, methylene blue and the like. However, these polymerization inhibitors shall inhibit polymerization unlike methoxyphenol, therefore, it is desired that the final content is as low as possible, which may be preferably 0 to 0.1 ppm by weight, and more preferably 0 ppm by weight (not higher than detection limit).

Although principal component of the monomer is acrylic acid and/or an acrylate salt, the acrylic acid and the acrylate salt have different molecular weight. Taking into consideration of this difference in molecular weight, the converted value based on acrylic acid is specified in the present invention. The converted value based on acrylic acid refers to ratio of weight the included aforementioned minor component per the weight of acrylic acid (weight ratio) as converted assuming that the acrylate salt is entirely the equimolar unneutralized acrylic acid. More specifically, for example, ratio of the included aforementioned minor component such as p-methoxyphenol (weight ratio) is specified on the basis of the weight after converting into acrylic acid (converted from 94 to 72) by way of converting sodium acrylate after the neutralization (molecular weight: 94) to acrylic acid (molecular weight: 72). When partially neutralized or completely neutralized acrylate salt is turned into the polymer in the particulate water absorbing agent following polymerization, the converted value based on acrylic acid may be determined through converting the partially neutralized or completely neutralized polyacrylate salt is assumed to be entirely the equimolar unneutralized polyacrylic acid. The aforementioned partial neutralization means that neutralization ratio is greater than 0 mol % but less than 100 mol %. The aforementioned complete neutralization means that the neutralization ratio is 100 mol %. The aforementioned unneutralization means that the neutralization ratio is 1 mol %.

In the present invention, examples of the method for obtaining the acrylic acid composition as a monomer include the following (A) to (D), but not limited thereto. Quantitative determination of the aforementioned component may be carried out with liquid chromatography or gas chromatography.

(A) a method in which commercially available acrylic acid or an aqueous solution thereof containing 200 ppm by weight or more p-methoxyphenol as a polymerization inhibitor is distilled to adjust the content of methoxyphenol (such as p-methoxyphenol (boiling point: 113-115° C./5 mm)) to be not higher than 200 ppm by weight;

(B) a method in which to acrylic acid or an aqueous solution thereof without containing methoxyphenol such as p-methoxyphenol as a polymerization inhibitor is added methoxyphenol in a predetermined amount according to the invention;

(C) a method in which methoxyphenol (p-methoxyphenol) is finally adjusted in the production step of acrylic acid to give a predetermined amount according to the present invention; and (D) a method in which acrylic acids having varying content of methoxyphenol (such as p-methoxyphenol) are blended to give a predetermined amount according to the present invention.

In the above paragraph (A), specific examples of the process for obtaining an acrylic acid composition include e.g., processes using distillation, crystallization, or adsorption through using an ion exchange resin. Commercially available acrylic acid may contain p-methoxyphenol in an amount of approximately 200 ppm by weight. In this respect, techniques of the purification of acrylic acid to eliminate impurities such as polymerization inhibitor, acrylic acid dimer and the like upon polymerization in production of the water absorbing resin, (JP-A No. H6-211934, JP-A No. H3-31306, European Patent No. 942014, European Patent No. 574260) have been also known. However, when acrylic acid is distilled upon polymerization, the difference in boiling points between acrylic acid and p-methoxyphenol suggests that content of p-methoxyphenol in acrylic acid after distillation is substantially non-detectable (ND/detection limit: 1 ppm by weight/determined with UV). In addition, according to a technique of adjusting the content in acrylic acid to be 10 to 160 ppm by weight (United States Patent Publication No. 2004/110914), the polymerization could be hardly controlled even though state of coloring of the water absorbing resin may be improved.

Therefore, according to the prior art in which a purification procedure of acrylic acid is applied which has been conventionally carried out in general for commercially available acrylic acid containing p-methoxyphenol in an amount of approximately 200 ppm by weight, there was no idea of adjusting to yield a predetermined amount of methoxyphenol falling within a specific range. For carrying out such adjustment, for example, any method as described in the above paragraphs (A) to (D) is required to be intentionally performed.

Moreover, acrylic acid which may be used as a monomer in the present invention is preferably acrylic acid containing 10 to 200 ppm methoxyphenol, and is more preferably acrylic acid having a content of phenothiazine being 0 to 0.1 ppm by weight, a content of at least one compound selected from the group consisting of aldehyde component other than furfural and maleic acid being 0 to 5 ppm by weight, and a content of at least one saturated carboxylic acid selected from the group consisting of acetic acid and propionic acid being 10 to 800 ppm by weight.

In the present invention, it is also preferable that the monomer component is polymerized in the presence of a predetermined amount of a solvent (toluene, diphenyl ether or the like) illustrated in Japanese Patent Application No. 2005-110960 (Application Date; Apr. 7, 2005). It is preferred that such a specified solvent is dissolved in acrylic acid beforehand. More specifically, in the present invention, a step of allowing radical polymerization of the monomer including a polymerization inactive organic compound having a dissolution parameter of $(1.0$ to $2.5) \times 10^4$ $(Jm^{-3})^{1/2}$ being 1 to 1000 ppm by weight is preferred.

(5) Alkali Treatment of Acrylic Acid

The method for the production of the water absorbing resin according to the present invention may also include a step of preparing a monomer component using the acrylic acid described above. In this instance, the acrylic acid matter may be preferably treated with an alkali.

This alkali treatment refers to subjecting acrylic acid to a neutralizing treatment at a certain temperature or higher (high-temperature neutralization) or at a certain neutralization ratio or greater (high neutralization) in neutralization of acrylic acid. Such an alkali treatment drastically accelerates the polymerization of acrylic acid. Illustrative specific examples of the process for this alkali treatment include, e.g., a process in which acrylic acid is gradually added to a certain amount of an alkali material to give a strong alkali region; a process in which acrylic acid and a basic material are mixed by line mixing so that the alkali treatment is performed simultaneously with neutralization, and the like.

The neutralization in the alkali treatment at a higher temperature than common neutralization temperature is also referred to as high-temperature neutralization. The alkali treatment is preferably conducted with high-temperature neutralization. Specifically, the temperature in the alkali treatment is preferably not lower than 30° C. but not higher than the boiling point of the aqueous acrylic acid solution, more preferably not lower than 40° C., still more preferably not lower than 50° C., and particularly preferably not lower than 60° C. When the temperature in the alkali treatment is low, polymerization capacity becomes very low even though purified acrylic acid is used in unneutralized case, which may also result in inferior physical properties.

The alkali treatment carried out in the state with the neutralization ratio of acrylic acid being beyond 100 mol %, i.e., in an alkaline excess state, is also referred to as high neutralization. The alkali treatment is preferably conducted with high neutralization. In the alkali treatment, particularly in strong alkali treatment, acrylic acid is treated such that the concentration of the acrylate salt following the neutralization becomes preferably 10 to 80% by weight, more preferably 20 to 60% by weight, still more preferably 30 to 50% by weight in an aqueous solution or water dispersion. The treatment time, particularly the treatment time when the alkali treatment is carried out in an alkaline excess state may be determined ad libitum to fall within the range of preferably 1 sec to 2 hrs, more preferably 5 sec to 1 hour.

Furthermore, the alkali treatment is conducted in the presence of oxygen for the sake of stability. The alkali treatment is carried out in the state in which the aqueous acrylic acid (salt) solution contains oxygen of preferably 0.5 to 20 ppm, more preferably 1 to 15 ppm, and still more preferably 1.5 to 10 ppm. When the amount of oxygen is too small, a problem with stability of the monomer in the alkali treatment may be caused. Therefore, the alkali treatment may be carried out preferably in an oxygen or air atmosphere, more preferably while bubbling and/or incorporating oxygen or air. The amount of oxygen can be measured with a dissolved oxygen analyzer (for example, diaphragm polarograph type). It is preferred that thus resulting monomer has a turbidity (specified by JIS K-0101) of not greater than 0.5.

(6) Basic Material

Illustrative examples of the basic material which may be used in the present invention include, e.g., carbonic acid (hydrogen) salt, hydroxide of an alkali metal, ammonia, organic amine and the like. In light of yellowing preventive characteristic, as the basic material preferred according to the present invention, an amine compound such as ammonia or organic amine may be illustrated. More preferable basic material is an acrylate ammonium salt and/or an amine salt, and still more preferably has a content of the acrylate ammonium salt and/or amine salt per the monomer component being 40 to 100 mol %. An example of the method for the production of a particulate water-absorbent core according to the present invention in which an acrylate ammonium salt is used includes a step of surface crosslinking by polymerizing a partially neutralized acrylate ammonium salt with a polymerization initiator, followed by drying, pulverizing and particle size selection.

Although an alkali metal salt may be used in combination for the neutralization, a neutralizing agent (sodium hydroxide, sodium carbonate or the like) having a specified iron content as illustrated in Japanese Patent Application No. 2005-111204 (Filing Date: Apr. 7, 2005) may be preferably used. More specifically, when an alkali metal salt is used, neutralization is preferably carried out with a basic compound that contains iron in an amount of 0.2 to 5 ppm by weight (on the basis of the basic compound except for the solvent). As the compound incorporated in the basic compound for allowing iron to be included, $Fe_2O_3$ is preferred.

(7) Monomer

As the monomer, acrylic acid and/or a salt thereof is used in the range as described above, but other monomer may be used in combination. When a monomer other than acrylic acid and/or a salt thereof is used, the monomer other than acrylic acid and/or a salt thereof may be used at a ratio of preferably 0 to 30 mol %, and more preferably 0 to 10 mol % in total amount of the acrylic acid and/or a salt thereof used as the principal component. By using the monomer other than acrylic acid and/or a salt thereof at a ratio as described above, absorption properties of finally obtained water absorbing resin (and water absorbing resin composition) may be even more improved, and also, the water absorbing resin (and water absorbing resin composition) can be obtained at an even lower cost.

Examples of the monomer which may be used in combination include e.g., monomers illustrated in United States patents and European Patents described later. Specific examples of the monomer which may be used in combination include e.g., water soluble or hydrophobic unsaturated monomers and the like. Examples of the water soluble or hydrophobic unsaturated monomer include methacryl acid, (anhydrous) maleic acid, fumaric acid, crotonic acid, itaconic acid, vinylsulfonic acid, 2-(meth)acrylamide-2-methylpropanesulfonic acid, (meth)acryloxyalkanesulfonic acid and alkali metal salts, ammonium salt thereof, N-vinyl-2-pyrrolidone, N-vinylacetoamide, (meth)acrylamide, N-isopropyl(meth)acrylamide, N,N-dimethyl(meth)acrylamide, 2-hydroxyethyl(meth)acrylate, methoxypolyethylene glycol (meth) acrylate, polyethylene glycol (meth)acrylate, isobutylene, lauryl(meth)acrylate and the like. The polymer according to the present invention may also involve those including the water soluble or hydrophobic unsaturated monomer as described above as a copolymerizing component.

Process for crosslinking which may be employed in the present invention is not particularly limited, but, examples thereof include e.g., a process of allowing crosslinking after adding the crosslinking agent during or after the polymerization; a process of allowing radical crosslinking with a radical polymerization initiator; a process of allowing radiation crosslinking with an electron beam or the like; and the like. However, a process in which polymerization is allowed by adding a certain amount of an internal crosslinking agent previously to the monomer, thereby permitting a crosslinking reaction concurrently or following the polymerization.

Examples of the internal crosslinking agent which may be used in the present invention include e.g., N,N'-methylenebisacrylamide, (poly)ethylene glycol di(meth)acrylate, (poly)propylene glycol di(meth)acrylate, (polyoxyethylene)trimethylolpropane tri(meth)acrylate, trimethylolpropane di(meth)acrylate, polyethylene glycol di(β-acryloyloxypropionate), trimethylolpropane tri(β-acryloyloxypropionate), poly(meth)allyloxyalkane, polyethylene glycol diglycidyl ether, ethylene glycol, polyethylene glycol, glycerin and the like. One or two or more of these internal crosslinking agents may be used. When one or more kinds of the internal crosslinking agents are used, it is preferred that a compound having 2 or more polymerizable unsaturated groups is essentially used in polymerization taking into consideration of absorption properties and the like of the resulting water absorbing resin.

The internal crosslinking agent may be used in an amount of preferably 0.005 to 2 mol %, more preferably 0.01 to 1 mol %, and still more preferably 0.05 to 0.2 mol % of the monomer as described above. When the using amount of the internal crosslinking agent is less than 0.005 mol %, or, more than 2 mol %, desired absorption properties may not be possibly achieved.

When reversed phase suspension polymerization or aqueous polymerization is carried out in the polymerization step, and when the monomer component is prepared to give an aqueous solution, concentration of the monomer component in this aqueous solution (hereinafter, referred to as aqueous monomer solution) is not particularly limited, but in light of the physical properties, the concentration is preferably 10 to 70% by weight, more preferably 15 to 65% by weight, and still more preferably 30 to 55% by weight. Additionally, when the aforementioned aqueous polymerization or reversed phase suspension polymerization is carried out, a solvent other than water may be used in combination as needed. Type of the solvent which may be used in combination is not particularly limited.

Moreover, upon polymerization, various physical properties of the water absorbing resin may be improved through adding a water soluble resin or a water absorbing resin, for example, 0 to 50% by weight, and preferably 0 to 20% by weight to the monomer. Furthermore, upon the polymerization, various physical properties of the water absorbing resin may be improved through adding any of a variety of foaming agents (carbonate, azo compound, bubble and the like), surfactants, chelating agents, chain transfer agents and the like in an amount of, for example, 0 to 5% by weight, preferably 0 to 1% by weight to the monomer.

(8) Polymerization Step

Polymerization of the monomer component which may be carried out in light of the aspect of performance and ease in controlling the polymerization is generally aqueous polymerization or reversed phase suspension polymerization in which the aforementioned monomer component is prepared to give an aqueous solution. Such polymerization may be performed also in an air atmosphere, preferably, it may be performed in an inert gas atmosphere such as nitrogen or argon (for example, oxygen being not more than 1%). Furthermore, the monomer component is preferably used for the polymerization after sufficiently displacing the dissolved oxygen with an inert gas (for example, oxygen: less than 1 ppm). In the present invention, aqueous polymerization which had been difficult to control although high productivity and excellent physical properties could be achieved is particularly suitable. Particularly preferable aqueous polymerization may be continuous belt polymerization, continuous polymerization or batch kneader polymerization.

The reversed phase suspension polymerization refers to a polymerization process in which an aqueous monomer solution is allowed to suspend in a hydrophobic organic solvent, and is described in, for example, U.S. Pat. Nos. 4,093,776, 4,367,323, 4,446,261, 4,683,274, 5,244,735 and the like. The aqueous polymerization refers to a polymerization process of an aqueous monomer solution without using a dispersion solvent, and is described in, for example, U.S. Pat. Nos. 4,625,001, 4,873,299, 4,286,082, 4,973,632, 4,985,518, 5,124,416, 5,250,640, 5,264,495, 5,145,906, 5,380,808 and the like, as well as European Patent Nos. 0811636, 0955086, 0922717, 1178059 and the like. The monomer, the crosslinking agent, the polymerization initiator, and other additives described in these United States patents and European Patents can be also applied to the present invention.

Moreover, in the present invention, for achieving improvement of the absorption properties and prevention of yellowing upon polymerization of the monomer, which are also involved in the problems to be solved by the present invention, total time from the time point of preparing the monomer component until initiation of the polymerization; total time from the time point of neutralization of acrylic acid until initiation of the polymerization; or total time from the time point of completing the neutralization of acrylic acid used as a principal component of the monomer until initiation of the polymerization may be preferably as short as possible. Such total time is preferably within 24 hrs, more preferably within 12 hrs, still more preferably within 3 hrs, and particularly preferably within 1 hour. Industrially, for carrying out the neutralization and preparation of the monomer component in large quantity in a tank, residence time, i.e., the aforementioned total time may be longer than 24 hrs in usual cases. However, it was found that longer time following preparation of the monomer component and/or longer time following the neutralization of acrylic acid (total time, described above) resulted in finding of increase in residual monomers and yellowing of the water absorbing resin. Hence, in attempts to shorten the residence time, preferably, continuous neutralization and continuous monomer component preparation are carried out, followed by carrying out batch-wise polymerization or continuous polymerization, more preferably continuous polymerization.

Examples of polymerization initiator which may be used upon polymerization of the aforementioned aqueous monomer solution include, e.g., persulfate salts such as potassium persulfate, ammonium persulfate and sodium persulfate;

t-butylhydroperoxide, hydrogen peroxide, 2,2'-azobis(2-amidinopropane) dihydrochloride, 2-hydroxy-1-phenyl-propane-1-one, benzoinmethyl ether and the like. Additionally, redox initiators and the like may be illustrated prepared using both such a polymerization initiator and a reducing agent that accelerates decomposition of the polymerization initiator in combination.

For achieving further prevention of yellowing in exemplary preferred methods for production in the present invention, employing a method for production is preferred in which an azo polymerization initiator such as 2,2-azobis(4-methoxy-2,4-dimethylvaleronitrile), 2,2-azobis(2,4-dimethylvaleronitrile), 2,2-azobis(2-methoxypropionenitrile), 2,2-azobis(2-methylbutyronitrile), 1,1-azobis(cyclohexane-1-carebonitrile), 2,2'-azobis(2-amidinopropane) dihydrochloride or the like is used among these polymerization initiators. In particular, a method for production in which a water soluble azo polymerization initiator is used is preferred. With respect to the azo polymerization initiator, any of the azo polymerization initiators described in U.S. Pat. No. 5,985,944, column 10, lines 17 to 35, and azo polymerization initiators commercially available from Wako Pure Chemical Industries, Ltd. can be used. Using amount of the aforementioned azo polymerization initiator is, in general, preferably 0.001 to 2 mol %, more preferably 0.01 to 1 mol %, and still more preferably 0.01 to 0.5 mol % per the monomer component.

Although the aforementioned azo polymerization initiator and other polymerization initiator may be used in combination, in light of coloring (yellowing) preventive characteristics, a persulfate salt such as potassium persulfate, ammonium persulfate or sodium persulfate may be used in an amount through controlling to fall within the range of preferably greater than 0 mol % but not greater than 0.6 mol %, more preferably greater than 0 mol % but not greater than 0.5 mol %, still more preferably greater than 0 mol % but not greater than 0.3 mol %, and particularly preferably 0 mol % but not greater than 0.1 mol %, particularly more preferably greater than 0 mol % but not greater than 0.05 mol %, and most preferably greater than 0 mol % but not greater than 0.01 mol % per the monomer component. When the azo polymerization initiator and other polymerization initiator are used in combination, the molar ratio to the azo polymerization initiator may be not greater than 1/1, preferably not greater than ½ mol, and still more preferably not greater than ¼. Use of excess persulfate salt may lead to deterioration of physical properties and coloring (yellowing), therefore, use in combination to fall within the aforementioned range is preferred. In addition, a UV initiator may be also used in combination in the range that is similar to the aforementioned initiators.

Furthermore, when polymerization is carried out using a persulfate salt or peroxide, combined use with the aforementioned reducing agent is preferred. Examples of the reducing agent include e.g., (bi)sulfurous acid (salts) such as sodium sulfite and sodium hydrogen sulfite, L-ascorbic acid (salts), reducing metal (salts) such as ferrous salts, amines and the like. Using amount of these reducing agents may be, in general, preferably 0.001 to 2 mol %, and more preferably 0.01 to 0.5 mol % per the monomer component.

Also, in place of use of the polymerization initiator, a polymerization reaction may be permitted by irradiating an active energy ray such as radiation, electron ray or ultraviolet ray to the reaction system. Furthermore, the active energy ray such as radiation, electron ray or ultraviolet ray, and the polymerization initiator may be also used in combination.

Moreover, the reaction temperature and the reaction time in the aforementioned polymerization reaction are not particularly limited, but may be optionally determined depending on type of the hydrophilic monomer and polymerization initiator, reaction temperature and the like. The reaction time of the polymerization reaction may be, in general, preferably within 3 hrs, more preferably within 1 hour, and still more preferably within 0.5 hrs. The reaction temperature in the polymerization reaction may be preferably not higher than 150° C., and more preferably 90 to 120° C. in terms of the peak temperature. In addition, water and acrylic acid which may be evaporated during the polymerization may be captured as needed, which may be preferably further subjected to recycling in the production step of the water absorbing resin.

(9) Drying Step

The hydrogel crosslinked polymer obtained in the polymerization step may be finely divided to have an average particle diameter of not greater than 5 mm, still more not greater than 2 mm, if necessary, using a gel pulverizer or the like as needed. The average particle diameter is specified by, for example, description in U.S. Pat. No. 5,478,879. Furthermore, it is dried under a specified temperature condition, and as needed, subjected to pulverization, classification, and further agglomeration, followed by surface crosslinking under a specified temperature condition. The water absorbing resin of the present invention has superior physical properties, and the physical properties may be further improved through subjecting to such steps.

In order to achieve lowering of the residual monomer and prevention of yellowing which are also the problem to be solved by the present invention, time period from completion of the polymerization (since when discharged from the polymerizer) until starting drying via the gel pulverizing step as needed is preferably as short as possible. More specifically, drying of the hydrogel crosslinked polymer after the polymerization is started (charged into a dryer) preferably within 1 hour, more preferably within 0.5 hour, and still more preferably within 0.1 n hour. Additionally, in order to achieve lowering of the residual monomer and low coloring, temperature of the hydrogel crosslinked polymer since completion of the polymerization until starting drying is regulated preferably 50 to 80° C., and more preferably 60 to 70° C.

In industrial field, because polymerization is carried out on a large scale, residence time following the polymerization may be ordinarily longer than 3 hours. This residence time following the polymerization means time period from completion of the polymerization until starting of the drying. It was found that as this residence time following the polymerization becomes longer, or, as the temperature during the residence time is farther out of the preferable range, the residual monomer is increased, and the coloring becomes noteworthy. Hence, continuous polymerization and continuous drying are preferably performed to permit shortening of the residence time.

According to the aforementioned drying step, the resin solid content is adjusted to fall within the range of preferably not lower than 80% by weight, more preferably 85 to 99% by weight, still more preferably 90 to 98% by weight, and particularly preferably 92 to 97% by weight. Value of the resin solid content is [100−(moisture content (% by weight))], and is determined on the basis of the weight loss in drying by heating 1 g of the resin powder or particles in a windless oven at 180° C. for 3 hrs. Further, the drying temperature is not particularly limited, but may falls within preferably the range of 100 to 300° C., and more preferably within the range of 150 to 250° C. As the drying method, any of the drying methods such as drying by heating, hot-air drying, drying under reduced pressure, infra-red drying, microwave drying, drying in a drum dryer, dehydration by azeotropy with a hydrophobic organic solvent, high humidity drying using water vapor at a high temperature and the like may be employed. Preferably, hot-air drying with a gas having a dew point of 40 to 100° C., and more preferably a dew point of 50 to 90° C. may be employed. In the present invention, the drying may be concomitantly carried out with the polymerization.

(10) Range of Particle Size Distribution after Drying and Adjustment Thereof

Dried water absorbing resin is obtained by drying the hydrogel polymer after the polymerization. The dry water absorbing resin may be directly used as dry powder (preferably solid content being not lower than 80%), and also, the range of particle size distribution may be adjusted after the drying as needed. The water absorbing resin after drying may be adjusted to have preferably a specified range of particle size distribution for improving the physical properties in the surface crosslinking described later. The range of particle size distribution may be adjusted ad libitum by polymerization, pulverization, classification, agglomeration, fine powder recovery and the like.

Weight average particle diameter (D50) before the surface crosslinking may be adjusted to 200 to 550 μm, preferably 250 to 500 μm, more preferably 300 to 450 μm, and particularly preferably 350 to 400 μm. Also, it is desired that amount of the particles of smaller than 150 μm may be as low as possible. Weight ratio of the particles of smaller than 150 μm to the total weight of the dry water absorbing resin may be adjusted to usually 0 to 5% by weight, preferably 0 to 3% by weight, and particularly preferably 0 to 1% by weight. In addition, amount of the particles not smaller than 850 μm is desirably as low as possible. Weight ratio of the particles not smaller than 850 μm to the total weight of the dry water absorbing resin may be adjusted to usually 0 to 5% by weight, preferably 0 to 3% by weight, and particularly preferably 0 to 1% by weight. Logarithmic standard deviation (σζ) of particle size distribution may be regulated to be preferably 0.20 to 0.40, preferably 0.27 to 0.37, and preferably 0.25 to 0.35.

(11) Surface Crosslinking Step

Next, the surface crosslinking according to the present invention will be further explained. The surface crosslinking of the water absorbing resin refers to providing a part having a higher crosslinking density on the surface layer (vicinity of the surface: usually, vicinity of not farther several 10 μm) of the water absorbing resin having a uniform cross-linked structure inside of the polymer. Although there are various crosslinking agents for carrying out the aforementioned surface crosslinking, in light of the physical properties, a crosslinking agent which can react with a carboxyl group, in general, a polyhydric alcohol compound, an epoxy compound, a polyvalent amine compound or a condensate thereof with a haloepoxy compound, an oxazoline compound, a mono-, di-, or polyoxazolidinone compound, a polyvalent metal salt, an alkylenecarbonate compound or the like may be used.

The surface crosslinking agent which may be used in the present invention is illustrated specifically in U.S. Pat. Nos. 6,228,930, 6,071,976, 6,254,990 and the like. Examples thereof include e.g., polyhydric alcohol compounds such as mono-, di, tri, tetra- or polyethylene glycol, monopropylene glycol, 1,3-propanediol, dipropylene glycol, 2,3,4-trimethyl-1,3-pentanediol, polypropylene glycol, glycerin, polyglycerin, 2-butene-1,4-diol, 1,4-butanediol, 1,3-butanediol, 1,5-pentanediol, 1,6-hexanediol and 1,2-cyclohexanedimethanol; epoxy compounds such as ethylene glycol diglycidyl ether and glycidol; polyvalent amine compounds such as ethylenediamine, diethylenetriamine, triethylenetetramine, tetraethylenepentamine, pentaethylenehexamine, polyethyleneimine and polyamide polyamine; haloepoxy compounds such as epichlorohydrin, epibromohydrin and α-methylepichlorohydrin; condensates of the aforementioned polyvalent amine compound and the aforementioned haloepoxy compound; oxazolidinone compounds such as 2-oxazolidinone; alkylene carbonate compounds such as ethylene carbonate; and the like, but particularly not limited thereto. In order to maximize the advantages of the present invention, it is preferred that at least a polyhydric alcohol is used among these crosslinking agents. A polyhydric alcohol having 2 to 10 carbon atoms, and preferably 3 to 8 carbon atoms may be used.

Using amount of the surface crosslinking agent may vary depending on the used compound, combination thereof and the like, but may fall within the range of preferably 0.001 parts by weight to 10 parts by weight, and more preferably 0.01 parts by weight to 5 parts by weight per 100 parts by weight of the solid content of the resin. In the present invention, water is preferably used for the surface crosslinking. In this process, the amount of water which may be used may vary depending on the moisture content of the used water absorbing resin, but preferably falls within the range of usually 0.5 to 20 parts by weight, and more preferably 0.5 to 10 parts by weight per 100 parts by weight of the water absorbing resin. Furthermore, in the present invention, a hydrophilic organic solvent may be used in addition to water. In this case, amount of the used hydrophilic organic solvent may fall within the range of usually 0 to 10 parts by weight, more preferably 0 to 5 parts by weight, and still more preferably 0 to 3 parts by weight per 100 parts by weight of the water absorbing resin. Temperature of the crosslinking agent solution may be preferably 0° C. to the boiling point, more preferably 5 to 50° C., and still more preferably 10 to 30° C. in light of the mixing performance and stability. Moreover, temperature of the water absorbing resin before the mixing may fall within the range of preferably 0 to 80° C., and more preferably 40 to 70° C. in light of the mixing performance.

A variety of methods of mixing can be employed for the method of mixing the surface crosslinking agent. Among these, a mixing method is preferred which includes premixing of water and/or a hydrophilic organic solvent and the surface crosslinking agent as needed, followed by spraying or dropwise addition of the aqueous solution to the water absorbing resin. Moreover, a mixing method is more preferred which includes premixing of water and/or a hydrophilic organic solvent and the surface crosslinking agent as needed, followed by spraying the aqueous solution to the water absorbing resin. Droplet size to be sprayed falls, preferably within the range of 1 to 300 μm, and more preferably within the range of 10 to 200 μm on the average. Additionally, upon the mixing, water insoluble fine particle powder and a surfactant may be allowed to coexist therewith in the range not to impair the advantage of the present invention, for example, 0 to 10% by weight or less, preferably 0 to 5% by weight, and more preferably 0 to 1% by weight. The surfactant which may be used and the using amount of the same are illustrated in International Patent Application No. WO2005 JP1689 (International Application Date: 2005 Feb. 4).

Mixing equipment which may be suitably used in the mixing is required to generate a great mixing force for ensuring homogenous mixing. Although any of a variety of mixers may be used as the mixing equipment which can be used in the present invention, preferably, a high speed agitation type mixer, and particularly a high speed agitation type continuous mixer is preferred. For example, trade name Turbulizer (manufactured by Hosokawa Micron International Inc., Japan), trade name Ledige mixer (manufactured by Ledige, Germany) or the like may be used.

The water absorbing resin after mixing with the surface crosslinking agent is preferably subjected to a heat treatment. Temperature upon carrying out the aforementioned heat treatment may be preferably 120 to 250° C., and more preferably 150 to 250° C. Heating time preferably falls within the range of 1 min to 2 hrs, and more preferably of 10 min to 1 hour. The heat treatment can be carried out using a common dryer or heating furnace. Examples of the dryer include e.g., grooved type dryer, rotary dryer, disk dryer, fluidized bed dryer, airflow type dryer, infra-red dryer and the like. Also, the water absorbing resin after heating may be cooled as needed.

These processes for surface crosslinking are also described in various European Patents such as European Patent Nos. 0349240, 0605150, 0450923, 0812873, 0450924 and 0668080, various Japanese Patents such as Japanese Patent Publication Nos. H7-242709 and 7-224304, various United States patents such as U.S. Pat. Nos. 5,409,771, 5,597,873, 5,385,983, 5,610,220, 5,633,316, 5,674,633 and 5,462,972, various International Patent Publications such as International Patent Publication Nos. WO99/42494, WO99/43720 and WO99/42496. These processes for surface crosslinking can be also applied to the present invention.

(12) Other Method for Production

In addition to the method for production as described above, the particulate water absorbing agent of the present invention can be also produced without using an ammonia salt or an amine salt, or without using an azo polymerization initiator. As such a method for production, methods for production which include a step of adding a compound including a phosphorus atom and/or a sulfur based reducing agent multiple times. In other words, as such a method for production, methods for production which include a step of adding a compound including a phosphorus atom and/or a sulfur based reducing agent at least two times. In this case, addition of the compound including a phosphorus atom and/or a sulfur based reducing agent may be carried out before, during or after the polymerization.

Examples of the method for production which includes a step of adding a compound including a phosphorus atom and/or a sulfur based reducing agent more than once include methods in which the following second to fourth methods for production are repeated multiple times. More specifically, illustrative methods employ at least two of the following production methods in combination: a production method in which a compound including a phosphorus atom and/or a sulfur based reducing agent is added upon preparation of the aqueous solution of the aforementioned monomer component to permit the polymerization (second method for production); a production method in which a compound including a phosphorus atom and/or a sulfur based reducing agent is added after completing the aforementioned polymerization step (third method for production); a production method in which a compound including a phosphorus atom and/or a sulfur based reducing agent is added after the surface crosslinking step and/or surface crosslinking step (fourth method for production). Details of the compound including a phosphorus atom and the sulfur based reducing agent will be described later.

In the production method in which a compound including a phosphorus atom and/or a sulfur based reducing agent is added upon preparation of the aqueous solution of the monomer component to permit the polymerization (second method for production), the particulate water absorbing agent is produced by carrying out the polymerization after addition of the compound including a phosphorus atom and/or a sulfur based reducing agent to the aforementioned monomer component, followed by the aforementioned drying step, and the range of particle size distribution adjustment step after drying to give a water absorbing resin, which is thereafter subjected to a surface crosslinking step.

Examples of the polymerization initiator which may be used include radical polymerization initiators such as potassium persulfate, ammonium persulfate, sodium persulfate, t-butylhydroperoxide, hydrogen peroxide and 2,2'-azobis(2-amidinopropane)dihydrochloride; and/or photopolymerization initiators such as 2-hydroxy-2-methyl-1-phenyl-propane-1-one. Taking into consideration of the physical properties of the water absorbing resin after the polymerization, these polymerization initiators may be used at a ratio of usually 0.001 to 2 mol %, and preferably 0.01 to 0.1 mol % of the entire monomer.

Amount of addition of the compound including a phosphorus atom and the sulfur based reducing agent may be usually 0.001 to 5% by weight, more preferably 0.01 to 3% by weight, and particularly preferably 0.01 to 1% by weight of the monomer component. Use beyond the above range is not preferred because deterioration of the water-absorption properties may be caused due to influences on the polymerization reaction. Use below the above range is not preferred because intended effect to prevent coloring may not be achieved.

In the production method in which a compound including a phosphorus atom and/or a sulfur based reducing agent is added after completing the polymerization step (third method for production), the particulate water absorbing agent is produced by adding the compound including a phosphorus atom and/or the sulfur based reducing agent to the hydrogel crosslinked polymer and mixed after completing the aforementioned polymerization step, followed by the aforementioned drying step, the range of particle size distribution adjustment step after drying, and then a surface crosslinking step. Amount of addition of the compound including a phosphorus atom and the sulfur based reducing agent may be usually 0.001 to 5% by weight, more preferably 0.01 to 3% by weight, and particularly preferably 0.01 to 1% by weight of the monomer component. Use beyond the above range is not preferred because the water-absorption properties may be deteriorated. Use below the above range is not preferred because intended effect to prevent coloring may not be achieved.

As the production method in which a compound including a phosphorus atom and/or a sulfur based reducing agent is added after the surface crosslinking step and/or surface crosslinking step (fourth method for production), a production method in which the compound including a phosphorus atom and/or the sulfur based reducing agent is added to the surface crosslinking agent in the surface crosslinking step of the water absorbing resin to permit the surface crosslinking; a production method in which the compound including a phosphorus atom and/or the sulfur based reducing agent is added following the surface crosslinking step; and the like may be illustrated. Amount of addition of the compound including a phosphorus atom and the sulfur based reducing agent may be usually 0.001 to 10% by weight, more preferably 0.01 to 5% by weight, and particularly preferably 0.01 to 3% by weight of the monomer component. Use beyond the above range is not preferred because the water-absorption properties may be deteriorated. Use below the above range is not preferred because intended effect to prevent coloring may not be achieved.

By using at least two of these second to fourth production methods in combination, excellent coloring preventive performance can be obtained, therefore, the particulate water absorbing agent of the present invention can be obtained without using an ammonia salt or an amine salt, or without using an azo polymerization initiator.

(13) Particulate Water Absorbing Agent

The particulate water absorbing agent of the present invention according to the aforementioned production method by way of example is a novel particulate water absorbing agent exhibiting novel performance not conventionally available.

Accordingly, the particulate water absorbing agent of the present invention is a particulate water absorbing agent comprising a water absorbing resin having a constitutional unit derived from acrylic acid and a salt thereof, and has the following (a) to (c). In the particulate water absorbing agent of the present invention, the surface crosslinking of the water absorbing resin is preferably perfected.

(a) Permeability potential under pressure (PPUP) being 50 to 100%.

(b) Yellowness index (YI) being 0 to 10, and rate of change of yellowness index (ΔYI) being 100 to 150% as measured with a coloring acceleration test for 14 days in an atmosphere of the temperature being 70±1° C. and the relative humidity being 95±1%.

(c) particles of smaller than 150 μm specified by standard sieve classification accounting for 0 to 5% by weight, weight average particle diameter (D50) specified by standard sieve classification being 200 to 550 μm, and logarithmic standard deviation (σζ) of particle size distribution specified by standard sieve classification being 0.20 to 0.40, wherein permeability potential under pressure (PPUP) is specified by the following formula:

PPUP(%)=(AAP:5.0 g)/(AAP:0.90 g)*100 wherein (AAP: 0.90 g) is the absorbency against pressure measured with 0.90 g of the particulate water absorbing agent for a 0.90% by weight aqueous sodium chloride solution under a pressure of 4.8 kPa for 60 min; and (AAP: 5.0 g) is the absorbency against pressure measured with 5.0 g of the particulate water absorbing agent for a 0.90% by weight aqueous sodium chloride solution under a pressure of 4.8 kPa for 60 min.

When the permeability potential under pressure (PPUP) of the particulate water absorbing agent is less than 50%, upon use in the absorbing article described later, particularly in the absorbing articles with an absorbent core having a water absorbing agent concentration of 40 to 100% by weight, diffusion of the liquid to be absorbed (urine and the like) across the entire absorbent core is prohibited. Hence, leakage from the absorbing article (diaper and the like) becomes liable to occur due to lowering of the efficiency of absorption. Further, when the yellowness index (YI) is beyond 10, or when rate of change of yellowness index ΔYI is beyond 150%, unsanitary impression is apt to be made to users (consumers) due to development of color change in the absorbing article (diaper and the like).

(a) PPUP

In the particulate water absorbing agent of the present invention, the permeability potential under pressure (PPUP) becomes preferably 50 to 100%, more preferably 60 to 100%, and most preferably 70 to 100%. The permeability potential under pressure is, unlike the absorbency against pressure (AAP: 0.9 g), a marker in connection with the stability of the absorbency against pressure (AAP) when the amount of the water absorbing resin (amount of the resin per unit area of the measurement) is increased from 0.90 g to 5.0 g. In other words, the permeability potential under pressure (PPUP) is, unlike the absorbency against pressure (AAP: 0.9 g), is a marker showing less lowering of the absorbency against pressure (AAP) when the amount of the water absorbing resin (amount of the resin per unit area of the measurement) is increased from 0.90 g to 5.0 g. This permeability potential under pressure (PPUP) is a novel parameter newly specified according to the spirit of the present invention.

For example, the present inventor found that the amount of the water absorbing resin (amount of the resin per unit area of the measurement) may partially vary in the diaper, and that the variation of the absorbency against pressure (AAP) resulting from alteration of the resin amount may be the grounds for deterioration of the physical properties of the diaper in practical applications. When (PPUP) specified by the method described in Example presented below is very high, superior physical properties are stably achieved in any amount (concentration) of the water absorbing resin in the diaper. Additionally, high liquid permeability may be also achieved. The permeability potential under pressure (PPUP) is described in detail in Japanese Patent Application No. 2005-109779 (filed on Apr. 6, 2005), and the disclosure of which is incorporated herein by reference.

(b) Yellowness Index (YI) and Rate of Change of Yellowness Index (ΔYI)

The particulate water absorbing agent of the present invention is less colored with almost no sallowness, and the time dependent stability (yellowing preventive characteristic) thereof is excellent. The particulate water absorbing agent of the present invention exhibits a YI value indicating the yellowness index of preferably 0 to 15, more preferably 0 to 13, still more preferably 0 to 10, and most preferably 0 to 5, with almost no sallowness. With respect of this YI value (Yellow Index), see, European Patent Nos. 942014 and 1108745. Moreover, rate of change of yellowness index specified in Example as determined after a coloring acceleration test at 70° C.±1, and under a relative humidity of 95±1% for 14 days is 100 to 150%, preferably 100 to 140%, more preferably 100 to 130%, and most preferably 100 to 120%. Thus, surprising yellowing preventive characteristic was exhibited even after exposure to an extreme condition.

(c) Range of Particle Size Distribution in Standard Sieve Classification

Weight average particle diameter (D50) of the particulate water absorbing agent of the present invention is adjusted to be 200 to 550 μm, preferably 250 to 500 μm, more preferably 300 to 450 μm, and particularly preferably 350 to 400 μm. Moreover, it is desired that amount of the particles of smaller than 150 μm may be as low as possible, and adjusted to usually 0 to 5% by weight, preferably 0 to 3% by weight, and particularly preferably 0 to 1% by weight. In addition, amount of the particles not smaller than 850 μm is desirably as low as possible, and adjusted to usually 0 to 5% by weight, preferably 0 to 3% by weight, and particularly preferably 0 to 1% by weight. Logarithmic standard deviation (σζ) of particle size distribution may be regulated to be preferably 0.20 to 0.40, preferably 0.25 to 0.37, and preferably 0.27 to 0.35. The standard sieve classification will be described later.

When the particulate water absorbing agent of the present invention is out of this particle size distribution, advantage in use for an absorbing article such as a disposable diaper or the like may be deteriorated. Such range of particle size distribution may be adjusted ad libitum by pulverization, classification, agglomeration, fine powder recovery and the like.

Furthermore, the particulate water absorbing agent of the present invention has a bulk density (specified by JIS K-3362) adjusted to fall within the range of preferably 0.40 to 0.90 g/ml, and more preferably 0.50 to 0.80 g/ml.

Additionally, in the particulate water absorbing agent of the present invention particles in between 600 to 150 μm may account for preferably 60 to 100% by weight, more preferably 70 to 100% by weight, and still more preferably 80 to 100% by weight of the total.

(d) Absorbency Against Pressure (AAP)

The particulate water absorbing agent according to the present invention has the absorbency against pressure (4.8 kPa: 0.90 g) for a physiological saline solution of preferably not less than 15 g/g, more preferably not less than 20 g/g, further preferably not less than 23 g/g, and still more preferably not less than 25 g/g. Also, absorbency against pressure (1.9 kPa: 0.90 g) for a physiological saline solution may be usually not less than 15 g/g, preferably not less than 20 g/g, further preferably not less than 25 g/g, more preferably not less than 28 g/g, and particularly preferably not less than 32 g/g. Although upper limit of the absorbency against pressure (4.8 kPa: 0.90 g) is not particularly defined, it may be usually approximately 60 g/g in light of balance with other physical properties and cost performance. Although upper limit of the absorbency against pressure (1.9 kPa: 0.90 g) is not particularly defined, it may be usually approximately 60 g/g in light of balance with other physical properties and cost performance. The absorbency against pressure herein is represented as "absorbency against pressure ($\alpha$: $\beta$)", wherein $\alpha$ represents pressure; and $\beta$ represents weight of the particulate water absorbing agent used in the measurement. Details of the method for measuring this absorbency against pressure will be described later.

(e) Centrifuge Retention Capacity (GVs) and Water Soluble Component

The particulate water absorbing agent of the present invention has a centrifuge retention capacity (GVs/also referred to as CRC) of preferably 10 to 50 g/g, more preferably 28 to 50 g/g, more preferably 28 to 45 g/g, more preferably 30 to 45 g/g, and particularly preferably 30 to 40 g/g. When CRC is too high, other physical properties not specified in the present invention such as gel strength, resistance to urine and the like may be deteriorated. In contrast, when CRC is too low, absorption capacity as a diaper may be insufficient in practical application. Additionally, the water extractable content may be preferably 0 to 25% by weight, more preferably 0 to 15% by weight, and still more preferably 0 to 10% by weight.

(f) Residual Monomer

Moreover, the particulate water absorbing agent of the present invention exhibits a residual monomer amount of preferably 0 to 400 ppm by weight, more preferably 0 to 300 ppm by weight, particularly preferably 0 to 200 ppm by weight, and especially 0 to 100 ppm. Such a residual monomer amount can be achieved through, for example, neutralization with ammonia, or use of an azo polymerization initiator.

(g) Other Additive

Furthermore, in accordance with the intended function, a compound including a phosphorus atom, a chelating agent, an oxidizing agent, a reducing agent, water an insoluble inorganic or organic powder such as silica or metal soap, a deodorant, an antimicrobial, macromolecular polyamine, pulp, thermoplastic fiber and the like may be added in an amount of 0 to 3% by weight, and preferably 0 to 1% by weight for the purpose of imparting any of various functions. Illustrative examples of the reducing agent include sulfur based reducing agents such as sulfurous acid (hydrogen) salts. Illustrative examples of the chelating agent include phosphorus based chelating agents, aminocarboxylic acids such as those described in U.S. Pat. No. 6,964,998, column 5 and column 25, and in U.S. Pat. No. 6,469,080, and the like. Details of the compound including a phosphorus atom and the sulfur based reducing agent will be described later.

The particulate water absorbing agent of the present invention may have a moisture content of not higher than 10% by weight, preferably beyond 0% by weight but not higher than 10% by weight, more preferably 2 to 10% by weight, more preferably 2 to 8% by weight, more preferably 2 to 7% by weight, more preferably 2 to 6% by weight, and particularly preferably 2 to 5% by weight. When the moisture content is out of this range, the water absorbing agent may be inferior in powder characteristics (flowability, conveying property, damage resistance).

In connection with the additives described hereinabove, they are described in detail in Japanese Patent Application No. 2005-109779 (filed on Apr. 6, 2005), and the disclosure of which is also incorporated herein by reference.

(14) Compound Including a Phosphorus Atom

Preferably, the particulate water absorbing agent of the present invention may contain a compound including a phosphorus atom. The compound including a phosphorus atom is effective in preventing coloring preventive and lowering of the YI value. Illustrative examples of the compound including a phosphorus atom include phosphorus chelating agents, phosphorus chain transfer agents, (phosphite) phosphate ester and the like. Illustrative examples of the phosphorus chelating agent include 1-hydroxyethylidene-1,1-diphosphonic acid, ethylenediamine tetra(methylenephosphonate), diethylenetriamine penta(methylenephosphonate) and/or salts thereof. Illustrative examples of the phosphorus chain transfer agent include sodium hypophosphite, potassium hypophosphite, calcium hypophosphite, barium hypophosphite, ammonium hypophosphite and the like. Illustrative examples of the (phosphite) phosphate ester include acid phosphoxyethyl methacrylate, acid phosphoxyethylene glycol monomethacrylate, methacroyloxyethyl acid phosphate monoethanolamine half salt, acid phosphoxypropylene glycol monomethacrylate, ethyldiethyl phosphonoacetate, monoethyl phosphate, mono n-butyl phosphate, mono n-octyl phosphate, mono n-lauryl phosphate, 2-acryloyloxyethyl acid phosphate and the like.

Preferably, the method for the production of a particulate water absorbing agent according to the present invention comprises a step of adding the aforementioned compound including a phosphorus atom. Method of adding the compound including a phosphorus atom is not particularly limited. More specifically, the compound including a phosphorus atom may be added during the polymerization, may be added after the polymerization, or may be added during and after the polymerization. Addition after the polymerization may be carried out before the drying step, or may be carried out after the drying step. Addition after the drying step may be carried out before adjusting the range of particle size distribution, may be carried out after adjusting the range of particle size distribution and before the surface crosslinking, may be carried out during the surface crosslinking, or may be carried out after the surface crosslinking. Also, the compound including a phosphorus atom may be added in multiple steps with divided aliquot. An example of the method for the production of a particulate water absorbing agent according to the present invention comprises a step of adding a phosphorus chelating agent to the water absorbing resin having PPUP falling within the above range. An example of the method for the production of a particulate water absorbing agent according to the present invention comprises a step of permitting polymerization after adding the phosphorus chelating agent to the monomer component before the polymerization. An example of the method for the production of a particulate water absorbing agent according to the present invention comprises a step of adding hypophosphorous acid to the water absorbing resin having PPUP falling within the above range.

(15) Sulfur Based Reducing Agent

Preferably, the particulate water absorbing agent of the present invention may contain a sulfur based reducing agent. The sulfur based reducing agent is effective in preventing coloring and in lowering of the YI value. Illustrative examples of the sulfur based reducing agent include sulfite salts such as sodium sulfite, potassium sulfite, calcium sulfite, zinc sulfite and ammonium sulfite; hydrogen sulfite salts such as sodium hydrogen sulfite, potassium hydrogen sulfite and ammonium hydrogen sulfite; pyrosulfite salts such as sodium pyrosulfite, potassium pyrosulfite and ammonium pyrosulfite; thiosulfate such as sodium thiosulfate, potassium thiosulfate and ammonium thiosulfate, and the like. In light of further improvement of the effect of lowering the YI value, hydrogen sulfite salts are preferred among the sulfur based reducing agents, and sodium hydrogen sulfite and potassium hydrogen sulfite are particularly preferred.

Preferably, the method for the production of a particulate water absorbing agent according to the present invention comprises a step of adding the aforementioned sulfur based reducing agent. Method of adding the sulfur based reducing agent is not particularly limited. More specifically, the sulfur based reducing agent may be added during the polymerization, may be added after the polymerization, or may be added during and after the polymerization. This addition after the polymerization may be carried out before the drying step, or may be carried out after the drying step. This addition after the drying step may be carried out before adjusting the range of particle size distribution, may be carried out after adjusting the range of particle size distribution and before the surface crosslinking, may be carried out during the surface crosslinking, or may be carried out after the surface crosslinking. Also, the sulfur based reducing agent may be added in multiple steps with divided aliquot.

(16) Usage

Usage of the particulate water absorbing agent of the present invention is not particularly limited. Preferably, the particulate water absorbing agent of the present invention can be used in absorbing articles such as disposable diapers, sanitary napkins, incontinence pads and the like. In particular, the particulate water absorbing agent of the present invention may be suitably used in highly dense diapers which have conventionally involved problems of the odor, coloring and the like derived from the raw material of the water absorbing agent. The highly dense diaper refers to the diaper in which a large quantity of a water absorbent resin is used in a piece of diaper. In particular, the particulate water absorbing agent of the present invention achieves particularly excellent performance when it is used in the upper layer part of the absorbent core in the absorbing article as described above. The upper layer part of the absorbent core is a part that faces human body in the usage state of the absorbing article.

The absorbing article of the present invention has the water absorbing agent, a front face sheet having liquid permeability, and a back face sheet having liquid impermeability. This absorbing article has an absorbent core obtained by forming with a hydrophilic fiber and the water absorbing agent to give a sheet shape as needed. When the hydrophilic fiber is not used, the absorbent core may be constituted by fixing the water absorbing agent on paper and/or nonwoven fabric. The absorbing articles of the present invention, in particular, disposable diapers for children, disposable diapers for adults and sanitary napkins can be fabricated by, for example, producing the absorbent core (absorbing core) through blending or sandwiching fiber substrate and the particulate water absorbing agent of the present invention, followed by sandwiching this absorbing core between a substrate with liquid permeability (the front face sheet) and a substrate with liquid non-permeability (the back sheet). Additionally, the absorbing article of the present invention may be further equipped with an elastic part, a diffusion layer, a pressure sensitive adhesive tape and the like, if necessary. Content of the particulate water absorbing agent per the absorbent core in this absorbing article (water absorbing agent concentration) may be preferably 30 to 100% by weight, preferably 40 to 100% by weight, more preferably 50 to 100% by weight, still more preferably 60 to 100% by weight, particularly preferably 70 to 100% by weight, and most preferably 75 to 95% by weight.

By allowing the content of the particulate water absorbing agent per the absorbent core in this absorbing article to fall within the above concentration range, advantage of the present invention may be further enhanced. For example, when the particulate water absorbing agent of the present invention is used in particularly the upper layer part of the absorbent core at the aforementioned concentration, excellent diffusibility of the liquid to be absorbed such as urine may be achieved owing to high liquid permeability (high permeability potential under pressure). Due to this excellent diffusibility, improvement of absorption capacity of the entire absorbing article by efficient liquid distribution in absorbing articles such as disposable diapers can be attained. In addition, when the particulate water absorbing agent of the present invention is used in particularly the upper layer part of the absorbent core at the aforementioned concentration, for example, absorbing articles with the absorbent core that keeps white-colored state accompanied by sanitary impression can be provided.

Furthermore, the aforementioned absorbent core is preferably subjected to compression molding to have the density of not less than 0.06 g/cc but not greater than 0.50 g/cc, and basis weight of not less than 0.01 $g/cm^2$ but not greater than 0.20 $g/cm^2$. Examples of the fiber base material which can be used include e.g., ground wood pulp, cotton linters, and hydrophilic fibers such as cross-linked cellulosic fibers, rayon fibers, cotton fibers, wool fibers, acetate fibers, vinylon fibers, and the like, which are preferably airlied.

EXAMPLES

The present invention will be explained by way of Examples below, however, the present invention should not be construed as limiting to the Examples. Moreover, various physical properties described in claims and Examples of the present invention were determined according to the following measurement method. Although the following measurement method is described in connection with a particulate water absorbing agent, measurement on the water absorbing resin is also performed through reading the result of the particulate water absorbing agent in terms of the water absorbing resin. Electrical equipments were always used under conditions of 200 V or 100 V and 60 Hz in Examples. In addition, the water absorbing resin composition and the water absorbing resin were used under conditions of 25° C. 2° C. and 50% RH (relative humidity), unless particularly specified. Reagents and tools exemplified in the measurement method and Examples described below may be substituted for equivalent products ad libitum.

(1) Centrifuge Retention Capacity (GVs/Gel Volume Saline)

A water absorbing resin of 0.2 g was uniformly put in a bag (60 mm×60 mm) made of unwoven fabric, and the bag was sealed, which was then immersed in 100 g of a 0.9% by weight aqueous sodium chloride solution (also referred to as physiological saline solution) at 25 (±3)° C. The bag was taken out 60 minutes later and subjected to dewatering for 3 minutes at 250 G using a centrifuge. Thereafter, the bag made of unwoven fabric was weighed to determine weight $W_1$ (g). Similar operation was carried out without using any particulate water absorbing agent, and thus resulting weight $W_2$ (g) was determined. Absorption capacity (g/g) was then calculated according to the following formula 1:

$$GVs=(W_1-W_2)/0.2-1. \quad \text{Formula 1}$$

(2) Amount of Water Soluble Polymer and Extractable Ratio

Hereinafter, amount of water soluble polymer may be abbreviated as extractable polymer content. Also, the water soluble polymer may be also referred to as extractables. The extractable ratio is a ratio (% by weight) of extractables in a particulate water absorbing agent.

In a 250-ml plastic vessel with a lid was weighed 184.3 g of a 0.90% by weight aqueous sodium chloride solution. To the aqueous solution was added 1.00 g of a particulate water absorbing agent. The mixture was stirred for 16 hours to extract the extractables in the resin. This extract liquid was filtrated using a sheet of filter paper (Advantec Toyo Kaisha, Ltd., trade name: (JIS P 3801, No. 2), thickness: 0.26 mm, retention particle size: 5 μm). Then 50.0 g of thus resulting filtrate was weighed for use as a solution for measurement.

First, titration was carried out on 184.3 g of a physiological saline solution (0.90% by weight aqueous sodium chloride solution) alone with a 0.1N aqueous NaOH solution to give the pH of 10. Thereafter, titration was carried out with a 0.1N aqueous HCl solution to give the pH of 2.7. Accordingly, blank titer ([bNaOH] ml, [bHCl] ml) was determined. Similar titration operation was carried out also on the solution for measurement as described above to determine titer ([NaOH] ml, [HCl] ml). For example, in case of the particulate water absorbing agent including a known quantity of acrylic acid and a salt thereof, extractable ratio in the water absorbing resin can be calculated according to the following formula 2 based on the average molecular weight of the monomer and the titer determined by the aforementioned operation. Principal component of the extractables which were thus extracted shall be the extracted water soluble polymer. When the average molecular weight of the monomer is unknown, the average molecular weight of the monomer can be calculated using the neutralization ratio determined by the titration. This neutralization ratio may be calculated according to the following formula 3.

Extractable ratio(% by weight)=0.1×(average molecular weight of monomer)×184.3×100×([HCl]−[bHCl])/1000/1.0/50.0  Formula 2

Neutralization ratio(mol %)=(1−([NaOH]−[bNaOH])/([HCl]−[bHCl]))×100  Formula 3

(3) Residual Monomer

In connection with residual monomer (residual acrylic acid (salt)) of the particulate water absorbing agent after drying, amount of the residual monomer (ppm) of the particulate water absorbing agent (versus particulate water absorbing agent) was also analyzed by an UV analysis on liquid chromatography of the filtrate after stirring for 2 hrs which had been separately prepared in the above paragraph (2). Further, the residual monomer of the hydrogel before drying was determined by a similar UV analysis on liquid chromatography of the filtrate obtained by stirring the finely divided hydrogel containing the resin solid content of about 500 mg, and then correcting with the solid content.

(4) Absorbency Against Pressure (AAP)

Absorption capacity was measured under a compression (under a load) for a physiological saline solution with reference to U.S. Pat. Nos. 6,228,930, 6,071,976 and 6,254,990. A predetermined load (1.9 kPa or 4.9 kPa) was applied on 900 mg of a particulate water absorbing agent according to the method described in the aforementioned United States patents. Weight of the physiological saline solution absorbed to the particulate water absorbing agent was determined from the measurement value indicated by the scale in a time dependent manner over 60 min. Similar operation was separately carried out without using any particulate water absorbing agent to derive a blank value by determining the measurement value of the weight, which was indicated by the scale 1, of the physiological saline solution 11 absorbed to, for example, the filter paper 7 and the like other than the particulate water absorbing agent. Next, correction by subtracting the blank value was carried out to derive the absorbency against pressure (g/g) at 1.9 kPa or 4.8 kPa by dividing the weight of the physiological saline solution 11 actually absorbed to the particulate water absorbing agent by the weight of the particulate water absorbing agent (0.9 g). The foregoing reference signs (scale 1, filter paper 7 and physiological saline solution 11) correspond to those described in U.S. Pat. No. 6,254,990. Of the absorbency against pressure (g/g) 1.9 kPa or 4.8 kPa, the absorbency against pressure at 4.8 kPa is also referred to as (AAP: 0.90 g) herein. Measurement method of this (AAP: 0.90 g) is specifically, as described below. In Tables presented later, this (AAP: 0.90 g) is represented as "AAP 4.8 kPa". Also, the aforementioned absorbency against pressure (g/g) at 1.9 kPa is represented as "AAP 1.9 kPa" in the Tables presented later. Measurement method of this "AAP 1.9 kPa" is similar to the following (AAP: 0.90 g) except that the pressure was changed from 4.8 kPa to 1.9 kPa.

(5) Absorbency Against Pressure (AAP) and Permeability Potential Under Pressure (PPUP)

A particulate water absorbing agent of 0.900 g was uniformly scattered on a 400-Mesh wire mesh made of stainless steel (mesh opening size: 38 μm) welded to the bottom end face of a plastic support cylinder with an inner diameter of 60 mm. A piston (cover plate), which has an outer diameter a little smaller than 60 mm, forms no gap against the inner surface of the support cylinder and can move up and down smoothly, was mounted on the scattered particulate water absorbing agent. The weight $W_5$ (g) of the support cylinder, the particulate water absorbing agent and the piston was measured. This weight $W_5$ (g) is a total weight of the support cylinder, the particulate water absorbing resin and the piston. A load adjusted such that a pressure of 4.8 kPa including the piston can be applied to the particulate water absorbing agent uniformly was mounted on the piston, thereby completing a set of measuring apparatus. A glass filter having a diameter of 90 mm and a thickness of 5 mm was placed in a Petri dish having a diameter of 150 mm, and a physiological saline solution (0.9% by weight aqueous sodium chloride solution) controlled at 25±2° C. was poured up to the same level as the upper surface of the glass filter. A sheet of filter paper having a diameter of 9 cm (No. 2, manufactured by Toyo Roshi Kaisha Ltd.) was placed on this glass filter so that the upper face of the glass filter was entirely wetted through allowing this filter paper to absorb the physiological saline solution, and then excess solution was removed.

The set of the measuring apparatus was placed on the wetted filter paper and the liquid absorption was allowed under the load. The liquid level was kept constant by adding the liquid when the liquid surface dropped lower than the upper surface of the glass filter. The set of the measuring apparatus was lifted up after an hour and weight $W_6$ (g) (total weight of the support cylinder, the swollen particulate water absorbing agent and the piston) excluding the load was measured. Thus, the absorbency against pressure (A) (g/g) was calculated from the weights $W_5$ (g) and $W_6$ (g) according to the following formula 6:

Absorbency Against Pressure$(A)(g/g)=(W_6-W_5)/$
weight of particulate water absorbing agent$(g)=$
$(W_6-W_5)/0.900$ Formula 6

This absorbency against pressure (A) is (AAP: 0.90 g) referred to herein.

Next, value of the absorbency against pressure (B) was determined by a similar operation to the measurement of absorbency against pressure (A) except that the amount of the particulate water absorbing agent was changed to 5.000 g. In this operation, samples having high absorbency against pressure (B) can result in extremely high level of the swollen water absorbing resin (or particulate water absorbing agent) layer, therefore, the support cylinder for use must afford enough height. This absorbency against pressure (B) is (AAP: 5.0 g) referred to herein. Using the absorbencies against pressure (A) (g/g) and (B) (g/g) determined by the operation described above, permeability potential under pressure (PPUP) can be determined by the following formula 7:

Permeability Potential Under Pressure (PPUP)(%)=
(absorbency against pressure$(B)$/absorbency
against pressure$(A))\times 100$ Formula (7)

(6) Mass Median Particle Size (D50) Specified by Standard Sieve Classification, Logarithmic Standard Deviation ($\sigma\zeta$) of Particle Size Distribution and Particles Smaller than 150 μm (% by weight)

According to International Publication No. WO2004/069404, the water absorbing resin (or particulate water absorbing agent) was subjected to sieving using JIS standard sieves having mesh opening size of 850 μm, 710 μm, 600 μm, 500 μm, 425 μm, 300 μm, 212 μm, 150 μm, 106 μm and 45 μm (JIS Z8801-1 (2000)) or sieves in conformity to these JIS standard sieves, and oversize percentages R were plotted on a logarithmic probability paper. Particle size corresponding to R=50% by mass was thus determined as mass median particle size (D50). Logarithmic standard deviation ($\sigma\zeta$) is represented by the following formula, wherein smaller value of $\sigma\zeta$ means narrower particle-size distribution:

$\sigma\zeta=0.5\times\ln(X_2/X_1)$ (wherein $X_1$ and $X_2$ are particle diameters for R=84.1% and R=15.9%, respectively).

Particles (% by weight) of smaller than 150 μm specified by standard sieve classification refers to ratio of the weight of the particles passed through 150 μm JIS standard sieve (JIS Z8801-1 (2000)) to the weight of the entire particulate water absorbing agent. The particles of smaller than 150 μm particle (% by weight) specified by standard sieve classification may be also referred to herein as merely "particles of smaller than 150 μm (% by weight)" or "150 μm pass (%)".

(7) Evaluation Coloring of Particulate Water Absorbing Agent (Yellowness Index/YI value)

Evaluation of coloring of a particulate water absorbing agent was carried out using a spectrometric calorimeter SZ-Σ80 COLOR MEASURING SYSTEM, manufactured by Nippon Denshoku Industries Co., Ltd. In the preset conditions for the measurement: reflection measurement was selected; attached powder/paste sample support having an internal diameter of 30 mm and a height of 12 mm was used; a standard round white board No. 2 for powder/paste was used as a standard; and a 30 Φ floodlight pipe was used. A particulate water absorbing agent in an amount of about 6 g was filled in an equipped sample support. Thus filling achieved about 60% filling of the equipped sample support. Under conditions at room temperature (20 to 25° C.) and humidity of 50 RH %, YI value (Yellow Index) on the surface was measured with the aforementioned spectrometric calorimeter. This value is "yellowness index before the exposure before exposure)" referred to in the following formula 8.

Also, other measure, i.e., object color (L, a, b) or WB (Hunter color) can be measured all together with the same apparatus by the same measurement method. Low coloring and approximating substantiality white color is suggested as L/WB is larger, and while a/b is smaller.

Subsequently, about 6 g of a particulate water absorbing agent was filled in the aforementioned paste sample support, and the paste sample support filled with the particulate water absorbing agent was exposed in a constant temperature and humidity chamber (manufactured by Tabai Espec Corporation, PLATINOUSLUCIFER, type PL-2G) regulated to provide an atmosphere at 70±1° C. and relative humidity of 90±1% for 14 days. This exposure corresponds to the coloring acceleration test for 14 days. After the exposure, YI value (Yellow Index) of the surface was measured with the aforementioned spectrometric calorimeter. This measurement value corresponds to the "(yellowness index after exposure)" represented by the following formula 8.

The rate of change of yellowness index is represented as rate of change (%) of YI between before and after leaving to stand for 14 days in the atmosphere at a temperature of 70±1° C. and a relative humidity of 95±1%, which was calculated by the following formula.

rate of change of yellowness index(%)=(yellowness
index after exposure)/(yellowness index before
exposure)$\times 100$ Formula 8

The rate of change of yellowness index (%) determined by the formula 8 is also referred to herein as $\Delta YI$.

(8) Evaluation of Absorbent Core

An absorbent core was produced for evaluating performances as an absorbent core, and subjected to evaluation on rewet amount and coloring stability of the absorbent core.

To begin with, a method for production of an absorbent core for evaluation is demonstrated below.

The water absorbing resin (or particulate water absorbing agent) described later in an amount of 3 parts by weight and 1 part by weight of crushed wood pulp were subjected to dry mixing using a mixer. Thus obtained mixture was then spread on a wire screen of 400-Mesh (mesh opening size: 38 μm) to form a web with a diameter of 90 mm. The web was pressed under a pressure of 196.14 kPa (2 kgf/cm$^2$) for 1 minute to obtain an absorbent core for evaluation with a basis weight of 0.05 g/cm$^2$.

Subsequently, a rewet amount in 10 min was evaluated according to the following method.

The absorbent core for evaluation was placed on the bottom of a Petri dish with an inner diameter of 90 mm made of stainless steel (SUS), and nonwoven fabric with a diameter of 90 mm was placed on this absorbent core for evaluation. Subsequently, 30 ml of a physiological saline solution was poured from above the nonwoven fabric, and absorption was allowed for 10 min in the state without load. The physiological saline solution is a 0.90% by weight aqueous sodium chloride solution. Thereafter, 30 sheets of filter paper having an external diameter of 90 mm (manufactured by Toyo Roshi Kaisha, Ltd., No. 2) total weight of which ($W_7$ (g)) had been measured beforehand were placed on the nonwoven fabric. Additionally, a piston and a weight were placed on the filter paper. Total weight of this piston and weight was 20 kg. The piston and weight had an external diameter of 90 mm. The piston and the weight were placed on the filter paper so as to apply the load uniformly on the absorbent core, nonwoven fabric and filter paper. The load was applied by the piston and weight for 5 min to permit absorption of rewet liquid into the filter paper. Weight of the 30 sheets of the filter paper ($W_8$ (g)) was then measured to determine the rewet amount in 10 min according to the following formula 9:

Rewet amount in 10 min(g)=$W_8$-$W_7$.  Formula 9 absorbent core evaluation

Furthermore, for evaluation of coloring of the absorbent core, thus resulting absorbent core was left to stand in the aforementioned constant temperature and humidity chamber under an atmosphere of 30±1° C. and a relative humidity of 90±1% for 60 days. Thereafter, observation of appearance was made. Results of evaluation of the appearance before and after leaving to stand for 60 days are shown in Table 1 and Table 2 below.

Production Example 1

Commercially available acrylic acid (Wako Pure Chemical Industries, Ltd., special grade chemical; containing 200 ppm p-methoxyphenol) obtained by gas phase catalytic oxidation was supplied to the bottom of a separation tower of high-boiling point impurities having 50 perforated plates without weir, distilled with a reflux ratio of 1, and further distilled again. Next, thereto was added p-methoxyphenol to 50 ppm by weight (vs. acrylic acid solid content) to give an acrylic acid composition (1). Any one of protoanemonin amount, furfural amount, β-hydroxypropionic acid amount and acrylic acid dimer amount in the acrylic acid composition (1) was "ND". "ND" means that ratio included in the acrylic acid composition (1) is less than 1 ppm by weight.

Production Example 2

In a 5-L five-neck flask equipped with two dropping funnels, a pH meter, a thermometer and an agitation blade was charged ion exchanged water. To five necks of the five-neck flask the aforementioned two dropping funnels, the pH meter, the thermometer and the agitation blade were equipped, respectively. Furthermore, to one dropping funnel of the two dropping funnels was fed the acrylic acid composition (1) at room temperature, while a 25% by weight aqueous ammonia solution was fed to another dropping funnel at room temperature. In this state, the 5-L flask was immersed in a water cooling bath. Next, while stirring the neutralization reaction system in the 5-L flask and keeping at not higher than 35° C., to the flask was added dropwise a 25% by weight aqueous ammonia solution and acrylic acid composition (1) simultaneously to give a 37% by weight aqueous ammonium acrylate solution (1).

Production Example 3

In a similar manner to Production Example 2 except that a 48% by weight aqueous sodium hydroxide solution was used in place of the 25% by weight aqueous ammonia solution to give a 37% by weight aqueous sodium acrylate solution (1).

Example 1

As a vessel for polymerization, a jacketed stainless double-arm kneader having an inner volume of 10 L and having the inner face thereof coated with Teflon was provided. "Teflon" is a registered trade name. The kneader has two sigma-type blades with a rotation diameter of 120 mm, and a lid for sealing the system. In this kneader, 948 g of the acrylic acid composition (1) obtained in Production Example 1, 3480 g of an aqueous ammonium acrylate solution (1) being the neutralization product thereof, 522 g of ion exchanged water, and 0.10 mol % polyethylene glycol diacrylate (vs. entire monomer) as an internal crosslinking agent were mixed to obtain an aqueous monomer solution having a neutralization ratio of 70 mol %. This polyethylene glycol diacrylate as an internal crosslinking agent has an average number of addition moles (n) of ethyleneoxide being 8.2. Moreover, the aqueous monomer solution was charged in the sigma-type double-arm kneader while keeping at 22° C., and in this kneader was further bubbled a nitrogen gas to conduct replacement with nitrogen so that dissolving oxygen in the system became not more than 1 ppm. Next, hot water was passed through the jacket to elevate the temperature of the aqueous monomer solution to 45° C. Thereafter, 50 g of an aqueous 2,2'-azobis(2-amidinopropane) dihydrochloride solution as a polymerization initiator was added thereto while stirring the aqueous monomer solution to initiate the polymerization. The added 2,2'-azobis(2-amidinopropane) dihydrochloride was 0.1 g/mol. Unit (g/mol) of the polymerization initiator shows the weight (g) of the polymerization initiator per 1 mol of the monomer. After a predetermined time lapsed since addition of the polymerization initiator, the polymerization was initiated. After initiating the polymerization, advance of the polymerization was allowed while finely dividing the generated polymerized gel. Finely divided hydrogel crosslinked polymer (1) having a diameter of about 1 to 2 mm was obtained by polymerization of additional 20 minutes after attaining to the peak temperature.

Thus resulting hydrogel polymer (1) was spread over a wire mesh having a mesh opening size of 850 μm, followed by hot-air drying with hot air at 180° C. having a dew point of 70° for 90 min. Then, the dried matter was pulverized with a vibrating mill, followed by further classification with a JIS 850 μm standard sieve to give a dry powder (1) of the passed matter (particle diameter: 300 μm, σζ=0.35, ratio of particles of smaller than 150 μm being 2% of the total). Subsequently, a surface crosslinking agent containing 100 parts by weight of the dry powder (1), 0.4 parts by weight of 1,4-butanediol, 0.6 parts by weight of propylene glycol, 3.0 parts by weight of ion exchanged water and 0.5 parts by weight of isopropanol was mixed by spraying. A particulate water absorbing agent (1) was obtained by additional heat treatment at 210° C. for 40 min. The parts by weight of 1,4-butanediol, propyleneglycol, ion exchanged water and isopropanol represent weight ratio per 100 parts by weight of the passed matter.

Example 2

A particulate water absorbing agent (2) was obtained by adding 0.1 parts by weight of silica (trade name: Aerosil 200) to 100 parts by weight of the particulate water absorbing agent (1) obtained in Example 1 followed by mixing.

Example 3

As a vessel for polymerization, a jacketed stainless double-arm kneader having an inner volume of 10 L and having the inner face thereof coated with Teflon was provided. The kneader has two sigma-type blades with a rotation diameter of 120 mm, and a lid for sealing the system. In this kneader, 376.3 g of the acrylic acid composition (1) obtained in Production Example 1, 3983 g of an aqueous sodium acrylate solution (1) being the neutralization product thereof, 640.7 g of ion exchanged water, and 0.10 mol % polyethylene glycol diacrylate (vs. entire monomer) as an internal crosslinking agent were mixed to obtain an aqueous monomer solution having a neutralization ratio of 75 mol %. This polyethylene glycol diacrylate as an internal crosslinking agent has an average number of addition moles (n) of ethyleneoxide being 8.2. Furthermore, 5.0 g of 1-hydroxyethylidene-1,1-diphosphonic acid was mixed with the aqueous monomer solution. Subsequently, the aqueous monomer solution was charged in the sigma-type double-arm kneader while keeping at 22° C., and in this kneader was further bubbled a nitrogen gas to conduct replacement with nitrogen so that dissolving oxygen in the system became not more than 1 ppm. Next, hot water was passed through the jacket, and an aqueous solution of 0.09 (g/mol) sodium persulfate and 0.005 (g/mol) L-ascorbic acid as a polymerization initiator was added thereto while stirring the aqueous monomer solution to initiate the polymerization. Unit (g/mol) of the polymerization initiator shows the weight (g) of the polymerization initiator per 1 mol of the monomer. After a predetermined time lapsed since addition of the polymerization initiator, the polymerization was initiated. After initiating the polymerization, advance of the polymerization was allowed while finely dividing the generated polymerized gel. Finely divided hydrogel crosslinked polymer (2) having a diameter of about 1 to 2 mm was obtained by polymerization of additional 20 minutes after attaining to the peak temperature.

Thus resulting hydrogel polymer (2) was spread over a wire mesh having a mesh opening size of 850 μm, followed by hot-air drying with hot air at 180° C. having a dew point of 70° for 90 min. Then, the dried matter was pulverized with a vibrating mill, followed by further classification with a JIS 850 μm standard sieve to give a dry powder (2) of the passed matter (particle diameter: 350 μm, σζ=0.35, ratio of particles of smaller than 150 μm being 1% by weight of the total). Subsequently, a surface crosslinking agent containing 100 parts by weight of the dry powder (2), 0.4 parts by weight of 1,4-butanediol, 0.6 parts by weight of propylene glycol, 3.0 parts by weight of ion exchanged water, 0.5 parts by weight of isopropanol and 1.0 part by weight of 1-hydroxyethylidene-1,1-diphosphonic acid was mixed by spraying. A particulate water absorbing agent (3) was obtained by additional heat treatment at 210° C. for 40 min. The parts by weight of 1,4-butanediol, propyleneglycol, ion exchanged water, isopropanol and 1-hydroxyethylidene-1,1-diphosphonic acid represent weight ratio per 100 parts by weight of the passed matter.

Comparative Example 1

As a vessel for polymerization, a jacketed stainless double-arm kneader having an inner volume of 10 L and having the inner face thereof coated with Teflon was provided. The kneader has two sigma-type blades with a rotation diameter of 120 mm, and a lid for sealing the system. The acrylic acid composition (1) obtained in Production Example 1 in an amount of 376.3 g, 3983 g of an aqueous sodium acrylate solution (2) being the neutralization product thereof, 640.7 g of ion exchanged water, and 0.10 mol % polyethylene glycol diacrylate (vs. entire monomer) as an internal crosslinking agent were mixed to obtain an aqueous monomer solution having a neutralization ratio of 75 mol %. This polyethylene glycol diacrylate as an internal crosslinking agent has an average number of addition moles (n) of ethyleneoxide being 8.2. Moreover, the aqueous monomer solution was charged in the sigma-type double-arm kneader while keeping at 22° C., and in this kneader was further bubbled a nitrogen gas to conduct replacement with nitrogen so that dissolving oxygen in the system became not more than 1 ppm. Next, hot water was passed through the jacket, and an aqueous solution of sodium persulfate (0.09 g/mol) and L-ascorbic acid (0.005 g/mol) as a polymerization initiator was added thereto while stirring the aqueous monomer solution to initiate the polymerization. Unit (g/mol) of the polymerization initiator shows the weight (g) of the polymerization initiator per 1 mol of the monomer. After a predetermined time lapsed since addition of the polymerization initiator, the polymerization was initiated. After initiating the polymerization, advance of the polymerization was allowed while finely dividing the generated polymerized gel. Finely divided comparative hydrogel polymer (1) having a diameter of about 1 to 2 mm was obtained by polymerization of additional 20 minutes after attaining to the peak temperature.

Thus resulting comparative hydrogel polymer (1) was spread over a wire mesh having a mesh opening size of 850 μm, followed by hot-air drying with hot air at 180° C. having a dew point of 700 for 90 min. Then, the dried matter was pulverized with a vibrating mill, followed by further classification with a JIS 850 μm standard sieve to give a comparative dry powder (1) of the passed matter (particle diameter: 300 μm, σζ=0.35, ratio of particles of smaller than 150 μm being 2% of the total). Subsequently, a surface crosslinking agent containing 100 parts by weight of the comparative dry powder (1), 0.4 parts by weight of 1,4-butanediol, 0.6 parts by weight of propylene glycol, 3.0 parts by weight of ion exchanged water and 0.5 parts by weight of isopropanol was mixed by spraying. A comparative particulate water absorbing agent (1) was obtained by additional heat treatment at 210° C. for 40 min. The parts by weight of 1,4-butanediol, propyleneglycol, ion exchanged water and isopropanol represent weight ratio per 100 parts by weight of the passed matter.

Example 4

The comparative hydrogel polymer (1) obtained in Comparative Example 1 was spread over a wire mesh having a mesh opening size of 850 μm, followed by hot-air drying with hot air at 180° C. having a dew point of 70° for 90 min. Then, the dried matter was pulverized with a vibrating mill, followed by further classification with a JIS 850 μm standard sieve to give a dry powder (3) of the passed matter (particle diameter: 300 μm, σζ=0.35, ratio of particles of smaller than 150 μm being 1% of the total). Subsequently, a surface crosslinking agent containing 100 parts by weight of the dry powder (3), 0.4 parts by weight of 1,4-butanediol, 0.6 parts by weight of propylene glycol, 3.0 parts by weight of ion exchanged water, 0.5 parts by weight of isopropanol and 1.0 part by weight of 1-hydroxyethylidene-1,1-diphosphonic acid was mixed by spraying, and a heat treatment was carried out at 210° C. for 40 min. After this heat treatment, a particulate water absorbing agent (4) was obtained by further mixing by spraying an additive solution containing 3.0 parts by weight of ion exchanged water, 0.5 parts by weight of isopropanol and 1.0 part by weight of 1-hydroxyethylidene-1,1-diphosphonic acid per 100 parts by weight of the mixture subjected to the heat treatment. The parts by weight of 1,4-butanediol, propyleneglycol, ion exchanged water, isopropanol and 1-hydroxyethylidene-1,1-diphosphonic acid represent weight ratio per 100 parts by weight of the passed matter.

Example 5

With 500 parts by weight of the comparative hydrogel polymer (1) obtained in Comparative Example 1 was mixed by spraying 10 parts by weight of aqueous sodium hydrogen sulfite solution having a density of 0.1% by weight. Thus resulting mixture was spread over a wire mesh having a mesh opening size of 850 μm, followed by hot-air drying with hot air at 180° C. having a dew point of 70° for 90 min. Then, the dried matter was pulverized with a vibrating mill, followed by further classification with a JIS 850 μm standard sieve to give a dry powder (4) as the passed matter from this sieve. This dry powder (4) had a particle diameter of 300 μm, $\sigma\zeta=0.35$, and a ratio of particles of smaller than 150 μm being 1% of the total. Subsequently, a surface crosslinking agent containing 100 parts by weight of the dry powder (4), 0.4 parts by weight of 1,4-butanediol, 0.6 parts by weight of propylene glycol, 3.0 parts by weight of ion exchanged water, 0.5 parts by weight of isopropanol and 1.0 part by weight of 1-hydroxyethylidene-1,1-diphosphonic acid was mixed by spraying to obtain a particulate water absorbing agent (5). The parts by weight of 1,4-butanediol, propyleneglycol, ion exchanged water, isopropanol and 1-hydroxyethylidene-1,1-diphosphonic acid represent weight ratio per 100 parts by weight of the passed matter.

Production Example 4

In a similar manner to Production Example 3 except that a commercially available acrylic acid (manufactured by Wako Pure Chemical Industries, Ltd., special grade chemical; containing 200 ppm p-methoxyphenol) was used in place of the acrylic acid composition (1) to give a 37% by weight aqueous sodium acrylate solution (3).

Comparative Example 2

As a vessel for polymerization, a jacketed stainless double-arm kneader having an inner volume of 10 L and having the inner face thereof coated with Teflon was provided. The kneader has two sigma-type blades with a rotation diameter of 120 mm, and a lid for sealing the system. A commercially available acrylic acid (manufactured by Wako Pure Chemical Industries, Ltd., special grade chemical; containing 200 ppm p-methoxyphenol) in an amount of 376.3 g, 3983 g of an aqueous sodium acrylate solution (3) being the neutralization product thereof which was obtained in Production Example 4, 640.7 g of ion exchanged water, and 0.10 mol % polyethylene glycol diacrylate (vs. entire monomer) as an internal crosslinking agent were mixed to obtain an aqueous monomer solution having a neutralization ratio of 75 mol %. This polyethylene glycol diacrylate as an internal crosslinking agent has an average number of addition moles (n) of ethyleneoxide being 8.2. Moreover, the aqueous monomer solution was charged in the sigma-type double-arm kneader while keeping at 22° C., and in this kneader was further bubbled a nitrogen gas to conduct replacement with nitrogen so that dissolving oxygen in the system became not more than 1 ppm. Next, hot water was passed through the jacket, and an aqueous solution of sodium persulfate (0.09 g/mol) and L-ascorbic acid (0.005 g/mol) as a polymerization initiator was added thereto while stirring the aqueous monomer solution to initiate the polymerization. Unit (g/mol) of the polymerization initiator shows the weight (g) of the polymerization initiator per 1 mol of the monomer. After a predetermined time lapsed since addition of the polymerization initiator, the polymerization was initiated. After initiating the polymerization, advance of the polymerization was allowed while finely dividing the generated polymerized gel. Finely divided comparative hydrogel polymer (2) having a diameter of about 1 to 2 mm was obtained by polymerization of additional 20 minutes after attaining to the peak temperature.

Thus resulting comparative hydrogel polymer (2) was spread over a wire mesh having a mesh opening size of 850 μm, followed by hot-air drying with hot air at 180° C. having a dew point of 70° for 90 min. Then, a comparative particulate water absorbing agent (2) was obtained by pulverizing the dried matter with a vibrating mill, followed by further classification with a JIS 850 μm standard sieve to give the passed matter.

[Results of Analyses of Particulate Water Absorbing Agent "Table 1 and Table 2"]

Results of analyses of the particulate water absorbing agent (1), the particulate water absorbing agent (2) and the comparative particulate water absorbing agent (1) obtained in the foregoings are shown in Table 1.

Results of analyses of the particulate water absorbing agent (3), the particulate water absorbing agent (4), the particulate water absorbing agent (5) and the comparative particulate water absorbing agent (2) obtained in the foregoings are shown in Table 2.

The particulate water absorbing agents (1) to (5) of the present invention have high permeability potential under pressure (PPUP) and low yellowness index (YI value), and are excellent in yellowing preventive characteristic ($\Delta YI$) because white color state of the particulate water absorbing agents was exhibited even though they were exposed to conditions at 70° C. and 95% RH, i.e., under high temperature and high humidity for 14 days.

Such particulate water absorbing agent of the present invention exhibits excellent effects when it is used in an absorbent core (for example, a disposable diaper), accompanied by low rewet amount (Re-Wet), showing white state of the appearance of the absorbent core which can provide a sanitary impression, and keeping the white color state even though it is left to stand in an environment at 30° C. and 90% RH in which a condition in storage during summer time was assumed for 60 days. Accordingly, it is a particulate water absorbing agent that is suitable for practical applications.

When the particulate water absorbing agent obtained according to the present invention is used in a thinner type absorbent core such as a diaper at a high concentration, very excellent absorption performance is exhibited as compared to conventional absorbent cores. Particularly, it is advantageous in that absorbent cores which are excellent in liquid permeability characteristic, less coloring and storage stability can be provided.

TABLE 1

Specification and Results of Evaluation of Examples and Comparative Examples

|  | Example 1 Particulate water absorbing agent (1) | Example 2 Particulate water absorbing agent (2) | Comparative Example 1 Comparative particulate water absorbing agent (1) |
|---|---|---|---|
| GVs (g/g) | 26 | 25 | 29 |
| Extractable polymer content (%) | 9 | 9 | 9 |

TABLE 1-continued

Specification and Results of Evaluation of Examples and Comparative Examples

|  | Example 1<br>Particulate water<br>absorbing agent (1) | Example 2<br>Particulate water<br>absorbing agent (2) | Comparative Example 1<br>Comparative particulate<br>water absorbing agent (1) |
|---|---|---|---|
| Amount of residual monomer (ppm) | 150 | 160 | 200 |
| D50 (μm) | 350 | 350 | 330 |
| 150 μm pass (%) | 1 | 1 | 3 |
| σζ | 0.34 | 0.34 | 0.41 |
| AAP1.9 kPa (g/g) | 28 | 27 | 28 |
| AAP4.8 kPa (g/g) | 26 | 24 | 22 |
| PPUP (%) | 88 | 90 | 48 |
| YI value before exposure | 5 | 5 | 13 |
| YI value after exposure for 14 days | 5.5 | 5.5 | 33 |
| Rate of change of yellowness index ΔYI(%) | 110 | 110 | 254 |
| Rewet amount in 10 min (g) | 5 | 5 | 7 |
| Appearance of absorbent core before leaving to stand | White | White | White, Yellow particles partially found |
| Appearance of absorbent core after leaving to stand for 60 days | White | White | Yellowish brown particles notable |

TABLE 2

Specification and Results of Evaluation of Examples and Comparative Examples

|  | Example 3<br>Particulate water<br>absorbing agent (3) | Example 4<br>Particulate water<br>absorbing agent (4) | Example 5<br>Particulate water<br>absorbing agent (5) | Comparative Example 2<br>Comparative particulate<br>water absorbing agent (2) |
|---|---|---|---|---|
| GVs (g/g) | 25 | 27 | 26 | 30 |
| Extractable polymer content (%) | 10 | 9 | 10 | 10 |
| Amount of residual monomer (ppm) | 180 | 190 | 170 | 200 |
| D50 (μm) | 400 | 380 | 370 | 380 |
| 150 μm pass (%) | 2 | 1 | 1 | 3 |
| σζ | 0.33 | 0.35 | 0.35 | 0.42 |
| AAP1.9 kPa (g/g) | 29 | 27 | 28 | 9 |
| AAP4.8 kPa (g/g) | 27 | 26 | 22 | 8 |
| PPUP (%) | 90 | 88 | 90 | 21 |
| YI value before exposure | 4 | 5 | 5 | 13 |
| YI value after exposure for 14 days | 5.7 | 5.9 | 5.7 | 22 |
| Rate of change of yellowness index ΔYI(%) | 143 | 118 | 114 | 169 |
| Rewet amount in 10 min (g) | 3 | 6 | 5 | 15 |
| Appearance of absorbent core before leaving to stand | White | White | White | White, Yellow particles partially found |
| Appearance of absorbent core after leaving to stand for 60 days | White | White | White | Yellowish brown particles notable |

INDUSTRIAL APPLICABILITY

The present invention relates to a particulate water absorbing agent, a method for production of the same, and a water-absorbent core and an absorbing article in which this particulate water absorbing agent is used. More particularly, the present invention relates to a particulate water absorbing agent and the like having excellent absorption ability in practical applications in absorbing articles such as diapers. The particulate water absorbing agent according to the present invention can be used in any water-absorbent cores and absorbing articles including absorbing articles such as disposable diapers and sanitary napkins as well as water retention agents for use in agriculture and horticulture water retention agent, industrial water cut-off materials, and the like.

The invention claimed is:

1. A particulate water absorbing agent which comprises a water absorbing resin having a constitutional unit derived from acrylic acid and a salt thereof, and has:
    (a) permeability potential under pressure (PPUP) being 50 to 100%;
    (b) yellowness index (YI) being 0 to 10, and rate of change of yellowness index (ΔYI) being 100 to 150% as measured with a coloring acceleration test for 14 days in an atmosphere of the temperature being 70±1° C. and the relative humidity being 95±1%; and
    (c) particles of smaller than 150 μm specified by standard sieve classification accounting for 0 to 5% by weight, weight average particle diameter (D50) specified by standard sieve classification being 200 to 550 μm, and logarithmic standard deviation (σζ) of particle size distribution specified by standard sieve classification being 0.20 to 0.40, wherein permeability potential under pressure (PPUP) is specified by the following formula:

PPUP(%)=(AAP:5.0 g)/(AAP:0.90 g)*100 wherein (AAP: 0.90 g) is the absorbency against pressure measured with 0.90 g of the particulate water absorbing agent for a 0.90% by weight aqueous sodium chloride solution under a pressure of 4.8 kPa for 60 min; and (AAP: 5.0 g) is the absorbency against pressure measured with 5.0 g of the particulate water absorbing agent for a 0.90% by weight aqueous sodium chloride solution under a pressure of 4.8 kPa for 60 min.

2. The particulate water absorbing agent according to claim 1 which comprises a compound including a phosphorus atom.

3. The particulate water absorbing agent according to claim 1 wherein said water absorbing resin is subjected to surface crosslinking.

4. The particulate water absorbing agent according to claim 1 wherein the particulate water absorbing agent further has (d) (AAP: 0.90 g) is 20 to 60 g/g.

5. The particulate water absorbing agent according to claim 1 wherein the particulate water absorbing agent further has (e) centrifuge retention capacity (GVs) for a 0.90% by weight aqueous sodium chloride solution is 10 to 50 g/g, and extractables in water account for 0 to 25% by weight.

6. The particulate water absorbing agent according to claim 1 wherein the particulate water absorbing agent further has (f) residual monomer is 0 to 300 ppm by weight.

7. The particulate water absorbing agent according to claim 1 wherein a content of phenothiazine in terms of the converted value based on acrylic acid is 0 to 0.1 ppm by weight, content of at least one compound selected from the group consisting of at least one aldehyde component other than furfural and maleic acid is 0 to 5 ppm by weight, and content of at least one saturated carboxylic acid selected from the group consisting of acetic acid and propionic acid is 10 to 800 ppm by weight.

8. An absorbent core for sanitary goods formed to include the particulate water absorbing agent according to claim 1 and a hydrophilic fiber.

9. The absorbent core according to claim 8 wherein the particulate water absorbing agent per total weight of the particulate water absorbing agent and the hydrophilic fiber is 40 to 100% by weight.

10. An absorbing article which comprises the absorbent core according to claim 8, a front face sheet having liquid permeability and a back face sheet having liquid impermeability.

* * * * *